(12) United States Patent
Slomczynska et al.

(10) Patent No.: US 9,051,309 B2
(45) Date of Patent: Jun. 9, 2015

(54) 3,5-DISUBSTITUTED-1,3,4-OXADIAZOL-2(3H)-ONES AND COMPOSITIONS AND METHODS FOR CONTROLLING NEMATODE PESTS

(71) Applicant: Monsanto Technology LLC, St. Louis, MO (US)

(72) Inventors: Urszula J. Slomczynska, Ballwin, MO (US); Matthew W. Dimmic, Wildwood, MO (US); William P. Haakenson, Jr., St. Louis, MO (US); Al S. Wideman, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 14/210,927

(22) Filed: Mar. 14, 2014

(65) Prior Publication Data

US 2014/0274690 A1  Sep. 18, 2014

Related U.S. Application Data

(60) Provisional application No. 61/788,273, filed on Mar. 15, 2013.

(51) Int. Cl.
  *C07D 413/04* (2006.01)
  *A01N 43/824* (2006.01)
  *A01N 43/82* (2006.01)

(52) U.S. Cl.
  CPC .............. *C07D 413/04* (2013.01); *A01N 43/82* (2013.01)

(58) Field of Classification Search
  CPC ............................. C07D 413/04; A01N 43/82
  See application file for complete search history.

(56) References Cited

U.S. PATENT DOCUMENTS

| | | | |
|---|---|---|---|
| 4,269,846 A | 5/1981 | Huang et al. | |
| 4,465,017 A | 8/1984 | Simmons | |
| 4,759,945 A | 7/1988 | Nemecek et al. | |
| 5,080,925 A | 1/1992 | Kouno | |
| 5,107,787 A | 4/1992 | Kouno | |
| 5,389,399 A | 2/1995 | Bazin et al. | |
| 5,554,445 A | 9/1996 | Struszczyk et al. | |
| 5,891,246 A | 4/1999 | Lund | |
| 5,918,413 A | 7/1999 | Otani et al. | |
| 6,255,319 B1 | 7/2001 | Jegham et al. | |
| 7,060,722 B2 | 6/2006 | Kitajima et al. | |
| 7,074,794 B2 | 7/2006 | Kitajima et al. | |
| 7,144,901 B2 | 12/2006 | Ohmoto et al. | |
| 2003/0087831 A1 | 5/2003 | Ohmoto et al. | |
| 2004/0204368 A1 | 10/2004 | Ohmoto et al. | |
| 2007/0004642 A1 | 1/2007 | Ohmoto et al. | |

FOREIGN PATENT DOCUMENTS

| | | | |
|---|---|---|---|
| DE | 1921522 | | 9/1970 |
| DE | 1921522 A | * | 9/1970 |
| WO | 9213451 A1 | | 8/1992 |
| WO | 9850383 A1 | | 11/1998 |
| WO | 2006044502 A2 | | 4/2006 |
| WO | 2009023721 A1 | | 2/2009 |
| WO | 2010093650 A1 | | 8/2010 |
| WO | 2012030887 A1 | | 3/2012 |
| WO | 2014008257 A3 | | 1/2014 |
| WO | 2014089219 A1 | | 6/2014 |

OTHER PUBLICATIONS

Mishra et al. International Journal of PharmTech Research 2009, 1, 1354-1365.*
Paulsrud et al. Seed Treatment, Oregon Pesticide Applicator Training Manual: Chapters 1-4, 2001, pp. 1-24.*
Kiss, L.E., et al., "Design, Synthesis, and Structure-Activity Relationships of 1,3,4-oxadiazol-2(3H)-ones as Novel FAAH Inhibitors," 2011, Med Chem Commun, 2:889-894.
Ohmoto, K., et al., "Design and Synthesis of New Orally Active Inhibitors of Human Neutrophil Elastase," 2001, Biorg Med Chem, 9:1307-1323, 19 pages.
Sherman, W.R., "5-Nitro-2-Furyl-substituted 1,3,4-Oxadiazoles, 1,3,4-Thiadiazoles, and 1,3,5-Triazines," 1961, JOC, 26:88-95.
Taniyama, H., et al., "Studies on Chemotherapeutics for *Mycobacterium tuberculosis*. XII. Synthesis and Antibacterial Activity of 2-γ-Pyridyl-1, 3, 4-oxadiazol-5-one and its Related Compounds," 1956, Yakugaku Zasshi, 76:1300-1303. Abstract.
International Search Report and Written Opinion issued in PCT/US2014/26985, Jul. 18, 2014, 12 Pages.

* cited by examiner

*Primary Examiner* — Joseph Kosack
*Assistant Examiner* — Matthew Coughlin
(74) *Attorney, Agent, or Firm* — Senniger Powers LLP; Molly B. Edwards

(57) ABSTRACT

Provided herein are new 3,5-disubstituted-1,3,4-oxadiazol-2 (3H)-ones and derivatives thereof that exhibit nematicidal activity and are useful, for example, in methods for the control of unwanted nematodes.

28 Claims, No Drawings

3,5-DISUBSTITUTED-1,3,4-OXADIAZOL-2(3H)-ONES AND COMPOSITIONS AND METHODS FOR CONTROLLING NEMATODE PESTS

REFERENCE TO RELATED APPLICATIONS

This application claims the benefit of U.S. Provisional Application Ser. No. 61/788,273, filed Mar. 15, 2013, the entire contents of which are incorporated herein by reference.

FIELD

Provided herein are new 3,5-disubstituted-1,3,4-oxadiazol-2(3H)-ones and derivatives thereof that exhibit nematicidal activity and are useful, for example, in methods for the control of unwanted nematodes.

BACKGROUND

Nematodes are active, flexible, elongate organisms that live on moist surfaces or in liquid environments, including films of water within soil and moist tissues within other organisms. Many species of nematodes have evolved to be very successful parasites of plants and animals and, as a result, are responsible for significant economic losses in agriculture and livestock.

Plant parasitic nematodes can infest all parts of the plant, including the roots, developing flower buds, leaves, and stems. Plant parasites can be classified on the basis of their feeding habits into a few broad categories: migratory ectoparasites, migratory endoparasites, and sedentary endoparasites. Sedentary endoparasites, which include root knot nematodes (*Meloidogyne*) and cyst nematodes (*Globodera* and *Heterodera*), can establish long-term infections within roots that may be very damaging to crops.

There is an urgent need in the industry for effective, economical, and environmentally safe methods of controlling nematodes.

SUMMARY

There is now provided a 3,5-disubstituted-1,3,4-oxadiazol-2(3H)-one of Formula I or a salt thereof,

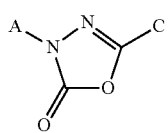

Formula I wherein A is selected from the group consisting of phenyl, pyridyl, pyrazyl, oxazolyl and isoxazolyl, each of which can be optionally independently substituted with one or more substituents selected from the group consisting of halogen, $CF_3$, $CH_3$, $OCF_3$, $OCH_3$, CN, and C(H)O; and C is selected from the group consisting of pyrrolyl, thienyl, furanyl, oxazolyl and isoxazolyl, each of which can be optionally independently substituted with one or more substituents selected from the group consisting of alkyl, alkoxy, cycloalkyl, haloalkyl, haloalkoxy, heterocyclyl, and halogen.

There is also provided a 3,5-disubstituted-1,3,4-oxadiazol-2(3H)-one of Formula II or a salt thereof,

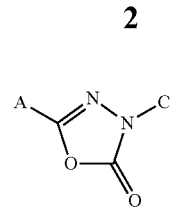

Formula II wherein A is selected from the group consisting of phenyl, pyridyl, pyrazyl, oxazolyl and isoxazolyl, each of which can be optionally independently substituted with one or more substituents selected from the group consisting of halogen, $CF_3$, $CH_3$, $OCF_3$, $OCH_3$, CN, and C(H)O; and C is selected from the group consisting of pyrrolyl, thienyl, furanyl, oxazolyl and isoxazolyl, each of which can be optionally independently substituted with one or more substituents selected from the group consisting of hydrogen, alkyl, alkoxy, cycloalkyl, haloalkyl, haloalkoxy, heterocyclyl, and halogen.

There is still further provided a 3,5-disubstituted-1,3,4-oxadiazol-2(3H)-one selected from the group consisting of: 3-phenyl-5-(thiophen-2-yl)-1,3,4-oxadiazol-2(3H)-one, 5-(furan-2-yl)-3-phenyl-1,3,4-oxadiazol-2(3H)-one, 3-(4-chlorophenyl)-5-(thiophen-2-yl)-1,3,4-oxadiazol-2(3H)-one, 3-phenyl-5-(pyrrol-1-yl)-1,3,4-oxadiazol-2(3H)-one, 3-(4-chlorophenyl)-5-(pyrrol-1-yl)-1,3,4-oxadiazol-2(3H)-one, 5-phenyl-3-(thiophen-2-yl)-1,3,4-oxadiazol-2(3H)-one, 3-(furan-2-yl)-5-phenyl-1,3,4-oxadiazol-2(3H)-one, and 5-(4-chlorophenyl)-3-(thiophen-2-yl)-1,3,4-oxadiazol-2(3H)-one.

There is also provided an aqueous nematicidal composition comprising a 3,5-disubstituted-1,3,4-oxadiazol-2(3H)-one as described herein.

There is also provided a seed comprising a coating comprising a 3,5-disubstituted-1,3,4-oxadiazol-2(3H)-one or nematicidal composition as described herein.

There is still further provided a method of controlling unwanted nematodes, the method comprising administering to mammals, birds, or their food, plants, seeds, or soil a composition comprising an effective amount of a 3,5-disubstituted-1,3,4-oxadiazol-2(3H)-one as described herein.

Other objects and features will be in part apparent and in part pointed out hereinafter.

DETAILED DESCRIPTION

Described herein are new 3,5-disubstituted-1,3,4-oxadiazol-2(3H)-ones and derivatives thereof that exhibit nematicidal activity. The compounds described herein may be used in the preparation of nematicidal compositions and in accordance with methods for control of unwanted nematodes, as set forth in detail below.

For example, in one embodiment, the compound is a 3,5-disubstituted-1,3,4-oxadiazol-2(3H)-one of Formula I or a salt thereof,

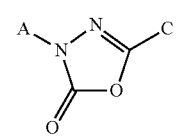

Formula I wherein A is selected from the group consisting of phenyl, pyridyl, pyrazyl, oxazolyl and isoxazolyl, each of which can be optionally independently substituted with one or more substituents selected from the group consisting of halogen, $CF_3$, $CH_3$, $OCF_3$, $OCH_3$, CN, and C(H)O; and C is selected from the group consisting of pyrrolyl, thienyl, furanyl, oxazolyl and isoxazolyl, each of which can be optionally independently substituted with one or more substituents selected from the group consisting of alkyl, alkoxy, cycloalkyl, haloalkyl, haloalkoxy, heterocyclyl, and halogen.

In one embodiment, A is phenyl, which may be optionally independently substituted with one or more substituents as described above. In one embodiment, C is selected from the group consisting of pyrrolyl, thienyl or furanyl, each of which can be optionally independently substituted as described above.

In some embodiments, C is optionally independently substituted with one or more substituents selected from the group consisting of F, Cl, Br, $CH_3$, and $OCF_3$.

For example, the compound may be a compound of Formula Ia or a salt thereof,

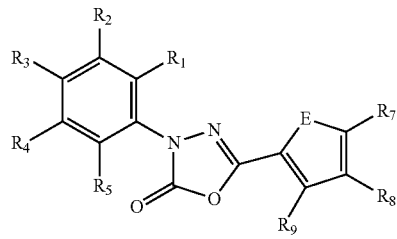

Formula Ia wherein $R_1$ and $R_5$ are independently selected from the group consisting of hydrogen, $CH_3$, F, Cl, Br, $CF_3$, and $OCF_3$; $R_2$ and $R_4$ are independently selected from the group consisting of hydrogen, F, Cl, Br, and $CF_3$; $R_3$ is selected from the group consisting of hydrogen, $CH_3$, $CF_3$, F, Cl, Br, $OCF_3$, $OCH_3$, CN, and C(H)O; $R_7$, $R_8$ and $R_9$ are independently selected from the group consisting of hydrogen, alkyl, alkoxy, cycloalkyl, haloalkyl, haloalkoxy, heterocyclyl, and halogen; E is selected from the group consisting of O, S, and N—$R_{10}$, wherein $R_{10}$ is alkyl.

In another embodiment $R_7$, $R_8$ and $R_9$ of Formula Ia are independently selected from the group consisting of hydrogen, F, Cl, Br, $CH_3$ and $OCF_3$.

Alternatively, the compound may be a compound of Formula Ib or a salt thereof,

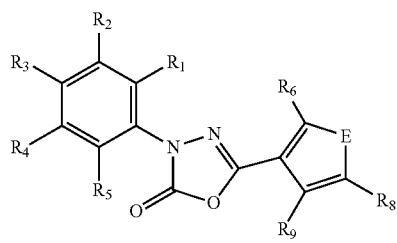

Formula Ib wherein $R_1$ and $R_5$ are independently selected from the group consisting of hydrogen, $CH_3$, F, Cl, Br, $CF_3$, and $OCF_3$; $R_2$ and $R_4$ are independently selected from the group consisting of hydrogen, F, Cl, Br, and $CF_3$; $R_3$ is selected from the group consisting of hydrogen, $CH_3$, $CF_3$, F, Cl, Br, $OCF_3$, $OCH_3$, CN, and C(H)O; $R_6$, $R_8$ and $R_9$ are independently selected from the group consisting of hydrogen, alkyl, alkoxy, cycloalkyl, haloalkyl, haloalkoxy, heterocyclyl, and halogen; E is selected from the group consisting of O, S, and N—$R_{10}$, wherein $R_{10}$ is alkyl.

In one embodiment, $R_6$, $R_8$ and $R_9$ of Formula Ib are independently selected from the group consisting of hydrogen, F, Cl, Br, $CH_3$ and $OCF_3$.

In another embodiment, the compound is a 3,5-disubstituted-1,3,4-oxadiazol-2(3H)-one of Formula Ic or a salt thereof,

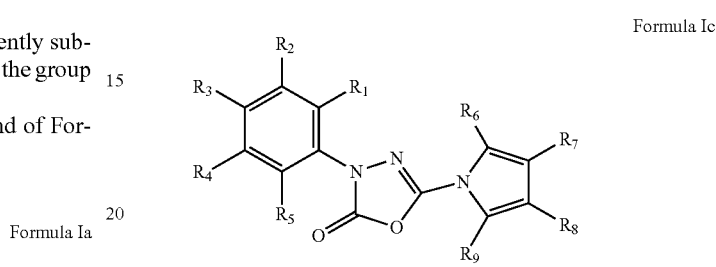

Formula Ic wherein $R_1$ and $R_5$ are independently selected from the group consisting of hydrogen, $CH_3$, F, Cl, Br, $CF_3$, and $OCF_3$; $R_2$ and $R_4$ are independently selected from the group consisting of hydrogen, F, Cl, Br, and $CF_3$; $R_3$ is selected from the group consisting of hydrogen, $CH_3$, $CF_3$, F, Cl, Br, $OCF_3$, $OCH_3$, CN, and C(H)O; and $R_6$, $R_7$, $R_8$ and $R_9$ are independently selected from the group consisting of hydrogen, alkyl, alkoxy, cycloalkyl, haloalkyl, haloalkoxy, heterocyclyl, and halogen.

In another embodiment, the compound is a 3,5-disubstituted-1,3,4-oxadiazol-2(3H)-one of Formula II or a salt thereof,

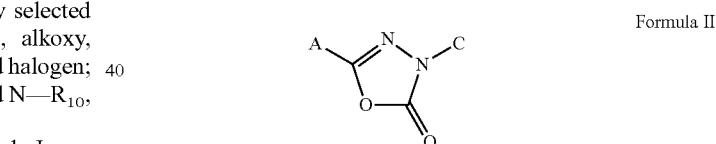

Formula II wherein A is selected from the group consisting of phenyl, pyridyl, pyrazyl, oxazolyl and isoxazolyl, each of which can be optionally independently substituted with one or more substituents selected from the group consisting of halogen, $CF_3$, $CH_3$, $OCF_3$, $OCH_3$, CN, and C(H)O; and C is selected from the group consisting of pyrrolyl, thienyl, furanyl, oxazolyl and isoxazolyl, each of which can be optionally independently substituted with one or more substituents selected from the group consisting of hydrogen, alkyl, alkoxy, cycloalkyl, haloalkyl, haloalkoxy, heterocyclyl, and halogen.

In one embodiment, A is phenyl, which may be optionally independently substituted with one or more substituents as described above. In an embodiment, C is selected from the group consisting of pyrrolyl, thienyl or furanyl, each of which can be optionally independently substituted as described above.

In some embodiments, C is optionally independently substituted with one or more substituents selected from the group consisting of F, Cl, Br, $CH_3$, and $OCF_3$.

For example, the compound may be a compound of Formula IIa or a salt thereof,

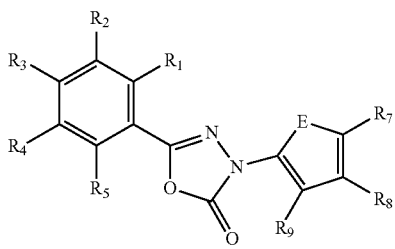

Formula IIa wherein $R_1$ and $R_5$ are independently selected from the group consisting of hydrogen, $CH_3$, F, Cl, Br, $CF_3$, and $OCF_3$; $R_2$ and $R_4$ are independently selected from the group consisting of hydrogen, F, Cl, Br, and $CF_3$; $R_3$ is selected from the group consisting of hydrogen, $CH_3$, $CF_3$, F, Cl, Br, $OCF_3$, $OCH_3$, CN, and C(H)O; $R_7$, $R_8$ and $R_9$ are independently selected from the group consisting of hydrogen, alkyl, alkoxy, cycloalkyl, haloalkyl, haloalkoxy, heterocyclyl, and halogen; E is selected from the group consisting of O, S, and $N-R_{10}$, wherein $R_{10}$ is alkyl.

In another embodiment, $R_7$, $R_8$, and $R_9$ of Formula IIa are independently selected from the group consisting of hydrogen, F, Cl, Br, $CH_3$, and $OCF_3$.

Alternatively, the compound may be a compound of Formula IIb or a salt thereof,

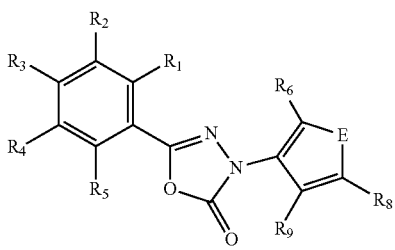

Formula IIb wherein $R_1$ and $R_5$ are independently selected from the group consisting of hydrogen, $CH_3$, F, Cl, Br, $CF_3$, and $OCF_3$; $R_2$ and $R_4$ are independently selected from the group consisting of hydrogen, F, Cl, Br, and $CF_3$; $R_3$ is selected from the group consisting of hydrogen, $CH_3$, $CF_3$, F, Cl, Br, $OCF_3$, $OCH_3$, CN, and C(H)O; $R_6$, $R_8$ and $R_9$ are independently selected from the group consisting of hydrogen, alkyl, alkoxy, cycloalkyl, haloalkyl, haloalkoxy, heterocyclyl, and halogen; E is selected from the group consisting of O, S, and $N-R_{10}$, wherein $R_{10}$ is alkyl.

In another embodiment $R_6$, $R_8$, and $R_9$ of Formula IIb are independently selected from the group consisting of hydrogen, F, Cl, Br, $CH_3$, and $OCF_3$.

As used herein, the term "halo" or "halogen" refers to any radical of fluorine, chlorine, bromine or iodine.

The term "alkyl" as employed herein, by itself or as part of another group, refers to both straight and branched chain radicals of up to ten carbons. Non-limiting examples of $C_1$-$C_{10}$ alkyl groups include methyl, ethyl, propyl, isopropyl, butyl, sec-butyl, tert-butyl, 3-pentyl, hexyl and octyl groups, each of which may be optionally independently substituted.

The term "haloalkyl" as employed herein, by itself or as part of another group, refers to an alkyl group, as defined herein, substituted with at least one halogen. Non-limiting examples of haloalkyl groups include trifluoromethyl and 2,2,2-trifluoroethyl.

The term "alkoxy" as employed herein, by itself or as part of another group, refers to an alkyl group, as defined herein, appended to the parent molecular moiety through an oxygen atom. Non-limiting examples of alkoxy groups include methoxy, ethoxy, propoxy, 2-propoxy, butoxy, tert-butoxy, pentyloxy, and hexyloxy, each of which may be optionally independently substituted.

The term "haloalkoxy" as employed herein, by itself or as part of another group, refers to an alkoxy group as defined herein, wherein the alkyl moiety of the alkoxy group is further substituted with at least one halogen. Non-limiting example of haloalkoxy groups include trifluoromethoxy, and 2,2-dichloroethoxy.

The term "cycloalkyl" as used herein refers to an alkyl group comprising a closed ring comprising from 3 to 8 carbon atoms. Non-limiting examples of cycloalkyl groups include cyclopropyl, cyclobutyl, cyclopentyl, cyclohexyl and cycloheptyl, each of which may be optionally independently substituted.

As used herein, the term "heterocyclyl," or heterocycle, refers to a saturated or partially saturated 3 to 7 membered monocyclic, or 7 to 10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on carbon or on a nitrogen atom if the resulting compound is stable. Non-limiting examples of common saturated or partially saturated heterocyclic groups include tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl, pyrazolinyl, tetronoyl and tetramoyl groups.

As used herein, the term "3,5-disubstituted-1,3,4-oxadiazol-2(3H)-one," or equivalently, "3,5-disubstituted-1,3,4-oxadiazol-2(3H)-one derivative," encompasses the compounds of Formulas I, Ia, Ib, Ic, II, IIa, and IIb as defined above.

Non-limiting examples of species of Formula Ia include 3-phenyl-5-(thiophen-2-yl)-1,3,4-oxadiazol-2(3H)-one of Formula Ia-i,

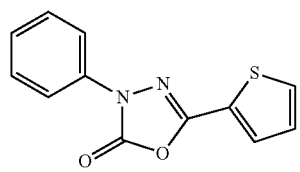

Formula Ia-i 5-(furan-2-yl)-3-phenyl-1,3,4-oxadiazol-2(3H)-one of Formula Ia-ii,

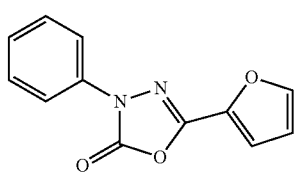

Formula Ia-ii 3-(4-chlorophenyl)-5-(thiophen-2-yl)-1,3,4-oxadiazol-2(3H)-one of Formula Ia-iii,

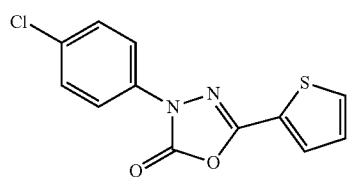

Formula Ia-iii and 3-(4-fluorophenyl)-5-(thiophen-2-yl)-1,3,4-oxadiazol-2(3H)-one of Formula Ia-iv.

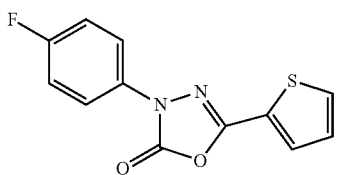

Formula Ia-iv 3-(4-chlorophenyl)-5-(furan-2-yl)-1,3,4-oxadiazol-2(3H)-one of Formula Ia-v,

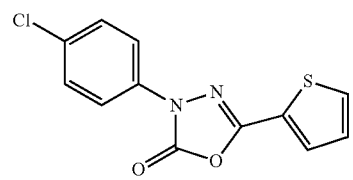

Formula Ia-v and 3-(4-chloro-2-methylphenyl)-5-(furan-2-yl)-1,3,4-oxadiazol-2(3H)-one of Formula Ia-v.

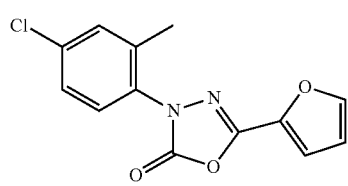

Formula Ia-vi

Non-limiting examples of species of Formula Ib include 3-phenyl-5-(thiophen-3-yl)-1,3,4-oxadiazol-2(3H)-one of Formula Ib-i,

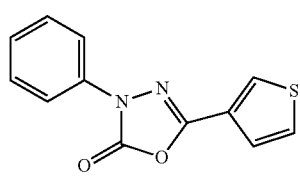

Formula Ib-i and 5-(furan-3-yl)-3-(phenyl)-1,3,4-oxadiazol-2(3H)-one of Formula Ib-ii.

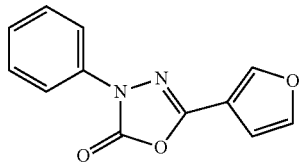

Formula Ib-ii

Non-limiting examples of species of Formula Ic include 3-phenyl-5-(1H-pyrrol-1-yl)-1,3,4-oxadiazol-2(3H)-one of Formula Ic-i,

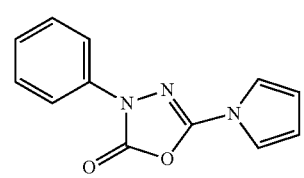

Formula Ic-i 3-(4-chlorophenyl)-5-(1H-pyrrol-1-yl)-1,3,4-oxadiazol-2(3H)-one of Formula Ic-ii.

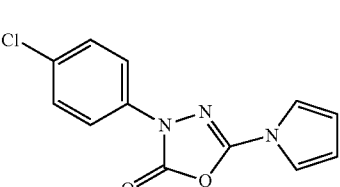

Formula Ic-ii

Non-limiting examples of species of Formula IIa include 5-phenyl-3-(thiophen-2-yl)-1,3,4-oxadiazol-2(3H)-one of Formula IIa-i,

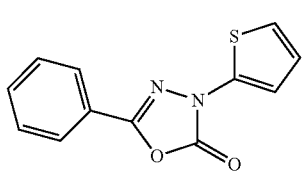

Formula IIa-i 3-(furan-2-yl)-5-phenyl-1,3,4-oxadiazol-2(3H)-one of Formula IIa-ii,

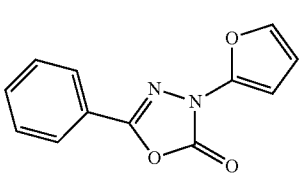

Formula IIa-ii 5-(4-chlorophenyl)-3-(thiophen-2-yl)-1,3,4-oxadiazol-2 (3H)-one of Formula IIa-iii,

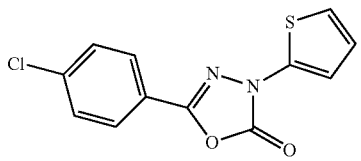

Formula IIa-iii and 5-(4-chlorophenyl)-3-(thiophen-2-yl)-1,3,4-oxadiazol-2 (3H)-one of Formula IIa-iv.

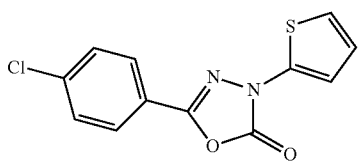

Formula IIa-iv

Non-limiting examples of species of Formula IIb include 5-phenyl-3-(thiophen-3-yl)-1,3,4-oxadiazol-2(3H)-one of Formula IIb-i,

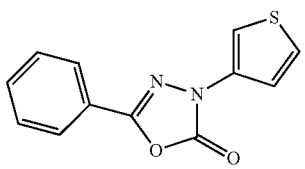

Formula IIb-i and 3-(furan-3-yl)-5-phenyl-1,3,4-oxadiazol-2(3H)-one of Formula IIb-ii.

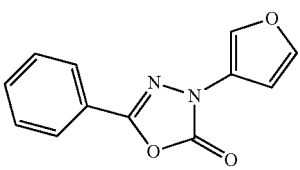

Formula IIb-ii

In one embodiment, the compound is a compound of one of Formulas Ia or IIa wherein each of $R_7$, $R_8$ and $R_9$ is hydrogen, a compound of Formula Ib or IIb wherein each of $R_6$, $R_8$ and $R_9$ is hydrogen, or a compound of Formula Ic wherein each of $R_6$, $R_7$, $R_8$ and $R_9$ is hydrogen. In some embodiments, each of $R_1$, $R_2$, $R_3$, $R_4$, and $R_5$ is also hydrogen. In other embodiments, at least one of $R_1$, $R_2$, $R_3$, $R_4$, and $R_5$ is other than hydrogen. For example, in some embodiments, at least one of $R_1$, $R_2$, $R_3$, $R_4$, and $R_5$ is halogen.

Methods of Use

Generally, the compounds described herein can be applied to seeds, plants, or the environment of plants needing nematode control, or to animals or the food of animals needing nematode parasite control.

For example, in one embodiment, the disclosure is generally related to a method for control of unwanted nematodes, the method comprising administering to mammals, birds, or their food, plants, seeds or soil a composition comprising an effective amount of a compound as described herein (e.g. 3,5-disubstituted-1,3,4-oxadiazol-2(3H)-one).

Application to Seeds

One embodiment of the disclosure is generally related to a method of protecting a seed, and/or the roots of a plant or plant parts grown from the seed, against damage by a nematode. In one embodiment, the method comprises treating a seed with a seed treatment composition comprising a compound as described herein (e.g. 3,5-disubstituted-1,3,4-oxadiazol-2(3H)-one) or a salt thereof.

The seed treatment methods described herein can be used in connection with any species of plant and/or the seeds thereof. In one embodiment, the methods are used in connection with seeds of plant species that are agronomically important. For example, the seeds can be of corn, peanut, canola/rapeseed, soybean, cucurbits, crucifers, cotton, beets, rice, sorghum, sugar beet, wheat, barley, rye, sunflower, tomato, sugarcane, tobacco, oats, as well as other vegetable and leaf crops. In some embodiments, the seed is corn, soybean, or cotton seed. The seed may be a transgenic seed from which a transgenic plant can grow and incorporates a transgenic event that confers, for example, tolerance to a particular herbicide or combination of herbicides, increased disease resistance, enhanced tolerance to stress and/or enhanced yield. Transgenic seeds include, but are not limited to, seeds of corn, soybean and cotton. The seed may comprise a breeding trait, including for example, a nematode breeding trait.

The seed treatment method comprises applying the seed treatment composition to the seed prior to sowing the seed, so that the sowing operation is simplified. In this manner, seeds can be treated, for example, at a central location and then distributed for planting. This may permit a person who plants the seeds to avoid the complexity and effort associated with handling and applying the seed treatment compositions, and to merely plant the treated seeds in a manner that is conventional for regular untreated seeds.

The seed treatment composition can be applied to seeds by any standard seed treatment methodology, including but not limited to mixing in a container (e.g., a bottle or bag), mechanical application, tumbling, spraying, immersion, and solid matrix priming. Seed coating methods and apparatus for their application are disclosed in, for example, U.S. Pat. Nos. 5,918,413, 5,891,246, 5,554,445, 5,389,399, 5,107,787, 5,080,925, 4,759,945 and 4,465,017, among others. Any conventional active or inert material can be used for contacting seeds with the seed treatment composition, such as conventional film-coating materials including but not limited to water-based film coating materials.

For example, in one embodiment, a seed treatment composition can be introduced onto or into a seed by use of solid matrix priming. For example, a quantity of the seed treatment composition can be mixed with a solid matrix material and then the seed can be placed into contact with the solid matrix material for a period to allow the seed treatment composition to be introduced to the seed. The seed can then optionally be separated from the solid matrix material and stored or used, or the mixture of solid matrix material plus seed can be stored or planted directly. Non-limiting examples of solid matrix materials which are useful include polyacrylamide, starch, clay, silica, alumina, soil, sand, polyurea, polyacrylate, or any other material capable of absorbing or adsorbing the seed treatment composition for a time and releasing the nematicide of the seed treatment composition into or onto the seed. It is useful to make sure that the nematicide and the solid matrix material are compatible with each other. For example, the solid matrix material should be chosen so that it can release the nematicide at a reasonable rate, for example over a period of minutes, hours, days, or weeks.

Imbibition is another method of treating seed with the seed treatment composition. For example, a plant seed can be directly immersed for a period of time in the seed treatment composition. During the period that the seed is immersed, the seed takes up, or imbibes, a portion of the seed treatment composition. Optionally, the mixture of plant seed and the seed treatment composition can be agitated, for example by shaking, rolling, tumbling, or other means. After imbibition, the seed can be separated from the seed treatment composition and optionally dried, for example by patting or air drying.

The seed treatment composition may be applied to the seeds using conventional coating techniques and machines, such as fluidized bed techniques, the roller mill method, rotostatic seed treaters, and drum coaters. Other methods, such as spouted beds may also be useful. The seeds may be pre-sized before coating. After coating, the seeds are typically dried and then transferred to a sizing machine for sizing. Such procedures are generally known in the art.

If the seed treatment composition is applied to the seed in the form of a coating, the seeds can be coated using a variety of methods known in the art. For example, the coating process can comprise spraying the seed treatment composition onto the seed while agitating the seed in an appropriate piece of equipment such as a tumbler or a pan granulator.

In one embodiment, when coating seed on a large scale (for example a commercial scale), the seed coating may be applied using a continuous process. Typically, seed is introduced into the treatment equipment (such as a tumbler, a mixer, or a pan granulator) either by weight or by flow rate. The amount of treatment composition that is introduced into the treatment equipment can vary depending on the seed weight to be coated, surface area of the seed, the concentration of the nematicide and/or other active ingredients in the treatment composition, the desired concentration on the finished seed, and the like. The treatment composition can be applied to the seed by a variety of means, for example by a spray nozzle or revolving disc. The amount of liquid may be determined by the assay of the formulation and the required rate of active ingredient necessary for efficacy. As the seed falls into the treatment equipment the seed can be treated (for example by misting or spraying with the seed treatment composition) and passed through the treater under continual movement/tumbling where it can be coated evenly and dried before storage or use.

In another embodiment, the seed coating may be applied using a batch process. For example, a known weight of seeds can be introduced into the treatment equipment (such as a tumbler, a mixer, or a pan granulator). A known volume of seed treatment composition can be introduced into the treatment equipment at a rate that allows the seed treatment composition to be applied evenly over the seeds. During the application, the seed can be mixed, for example by spinning or tumbling. The seed can optionally be dried or partially dried during the tumbling operation. After complete coating, the treated sample can be removed to an area for further drying or additional processing, use, or storage.

In an alternative embodiment, the seed coating may be applied using a semi-batch process that incorporates features from each of the batch process and continuous process embodiments set forth above.

In still another embodiment, seeds can be coated in laboratory size commercial treatment equipment such as a tumbler, a mixer, or a pan granulator by introducing a known weight of seeds in the treater, adding the desired amount of seed treatment composition, tumbling or spinning the seed and placing it on a tray to thoroughly dry.

In another embodiment, seeds can also be coated by placing the known amount of seed into a narrow neck bottle or receptacle with a lid. While tumbling, the desired amount of seed treatment composition can be added to the receptacle. The seed is tumbled until it is coated with the treatment composition. After coating, the seed can optionally be dried, for example on a tray.

In some embodiments, the treated seeds may also be enveloped with a film overcoating to protect the nematicidal coating. Such overcoatings are known in the art and may be applied using conventional fluidized bed and drum film coating techniques. The overcoatings may be applied to seeds that have been treated with any of the seed treatment techniques described above, including but not limited to solid matrix priming, imbibition, coating, and spraying, or by any other seed treatment technique known in the art.

Application to Plants and/or Soil

Another embodiment of the disclosure is generally related to protecting a plant against damage by a nematode. For example, in one embodiment, a treatment composition comprising a compound as described herein (e.g. 3,5-disubstituted-1,3,4-oxadiazol-2-(3H)-one) or a salt thereof, is supplied to a plant exogenously. Typically, the treatment composition is applied to the plant and/or the surrounding soil through sprays, drips, and/or other forms of liquid application.

In one embodiment, a treatment composition comprising a compound as described herein (e.g. 3,5-disubstituted-1,3,4-oxadiazol-2-(3H)-one) or a salt thereof, is directly applied to the soil surrounding the root zone of a plant. Soil applications may require 0.5 to 2 kg per hectare on a broadcast basis (rate per treated area if broadcast or banded).

The application may be performed using any method or apparatus known in the art, including but not limited to hand sprayer, mechanical sprinkler, or irrigation, including drip irrigation.

For example, in one embodiment, the nematicidal treatment composition is applied to plants and/or soil using a drip irrigation technique. Preferably, the nematicidal treatment composition is applied directly to the base of the plants or the soil immediately adjacent to the plants. The composition may be applied through existing drip irrigation systems. This procedure is particularly preferred for use in connection with cotton, strawberries, tomatoes, potatoes, vegetables, and ornamental plants.

In another embodiment, the nematicidal treatment composition is applied to plants and/or soil using a drench application. Preferably, a sufficient quantity of the nematicidal treatment composition is applied such that it drains through the soil to the root area of the plants. The drench application technique is particularly preferred for use in connection with crop plants, turf grasses, and animals.

In some embodiments, the nematicidal composition is applied to soil after planting. In other embodiments, however, the nematicidal composition may be applied to soil during planting. In other embodiments, however, the nematicidal composition may be applied to soil before planting. When the nematicidal composition is applied directly to the soil, it may be applied using any method known in the art. For example, it may be tilled into the soil or applied in furrow.

Administration to Animals

Another embodiment of the disclosure is generally related to a method of controlling unwanted nematodes, the method comprising administering to an animal a nematicidal treatment composition comprising a compound (e.g., a 3,5-disubstituted-1,3,4-oxadiazol-2(3H)-one or derivative thereof) as described herein. For example, in one embodiment, the nematicidal treatment composition may be administered to an animal orally to promote activity against internal parasitic nematodes. In another embodiment, the nematicidal treatment composition may be administered by injection of the host animal. In another embodiment, the nematicidal treatment composition may be administered to the host animal by topical application.

In some embodiments, the nematicidal composition is formulated for topical applications such as pour-ons, or for the use in tags or collars. In these embodiments, it is particularly preferred that the host animal is a non-human animal.

The nematicidal compositions described herein can be applied to any vertebrate animal (e.g., a bird or a mammal). The bird can be a domesticated fowl (e.g., a chicken, turkey, duck, or goose). The mammal can be a domesticated animal, e.g., a companion animal (e.g., a cat, dog, horse or rabbit) or livestock (e.g., a cow, sheep, pig, goat, alpaca or llama). Alternatively, the mammal can be a human.

Another embodiment of the disclosure is generally related to a nematicidal feed for a non-human vertebrate, wherein the nematicidal feed comprises (a) a feed; and (b) a nematicidal composition comprising a compound as described herein (e.g. 3,5-disubstituted-1,3,4-oxadiazole-2(3H)-one) or a salt thereof. In some embodiments, the feed is selected from the group consisting of: soy, wheat, corn, sorghum, millet, alfalfa, clover, and rye. Another embodiment is directed to a method of supplementing an animal feed to include one or more of the compounds as described herein (e.g. 3,5-disubstituted-1,3,4-oxadiazole-2(3H)-one) or salts thereof.

Treated Seeds

Another embodiment of the general disclosure is related to a seed that has been treated with a seed treatment composition comprising a compound as described herein. In some embodiments, the seed has been treated with the seed treatment composition using one of the seed treatment methods set forth above, including but not limited to solid matrix priming, imbibition, coating, and spraying. The seed may be of any plant species, as described above.

The treated seeds comprise the compound in an amount of at least about 0.1 mg/seed, from about 0.1 to about 2 mg/seed, from about 0.1 to about 1 mg/seed, and from about 0.1 to about 0.5 mg/seed.

Nematicidal Compositions

Another embodiment of the disclosure is generally related to a nematicidal composition comprising an effective amount of an 3,5-disubstituted-1,3,4-oxadiazol-2(3H)-one or derivative thereof as described herein. In some embodiments, the nematicidal composition may be an aqueous composition.

Generally, the nematicidal compositions described herein can comprise any adjuvants, excipients, or other desirable components known in the art. For example, in some embodiments, the nematicidal composition further comprises a surfactant.

Examples of anionic surfactants include alkyl sulfates, alcohol sulfates, alcohol ether sulfates, alpha olefin sulfonates, alkylaryl ether sulfates, arylsulfonates, alkylsulfonates, alkylaryl sulfonates, sulfosuccinates, mono- or diphosphate esters of polyalkoxylated alkyl alcohols or alkyl phenols, mono- or disulfosuccinate esters of alcohols or polyalkoxylated alkanols, alcohol ether carboxylates, phenol ether carboxylates. In one embodiment, the surfactant is an alkylaryl sulfonate.

Non-limiting examples of commercially available anionic surfactants include sodium dodecylsulfate (Na-DS, SDS), MORWET D-425 (a sodium salt of alkyl naphthalene sulfonate condensate, available from Akzo Nobel), MORWET D-500 (a sodium salt of alkyl naphthalene sulfonate condensate with a block copolymer, available from Akzo Nobel), sodium dodecylbenzene sulfonic acid (Na-DBSA) (available from Aldrich), diphenyloxide disulfonate, naphthalene formaldehyde condensate, DOWFAX (available from Dow), dihexylsulfosuccinate, and dioctylsulfosuccinate, alkyl naphthalene sulfonate condensates, and salts thereof.

Examples of non-ionic surfactants include sorbitan esters, ethoxylated sorbitan esters, alkoxylated alkylphenols, alkoxylated alcohols, block copolymer ethers, and lanolin derivatives. In accordance with one embodiment, the surfactant comprises an alkylether block copolymer.

Non-limiting examples of commercially available non-ionic surfactants include SPAN 20, SPAN 40, SPAN 80, SPAN 65, and SPAN 85 (available from Aldrich); TWEEN 20, TWEEN 40, TWEEN 60, TWEEN 80, and TWEEN 85 (available from Aldrich); IGEPAL CA-210, IGEPAL CA-520, IGEPAL CA-720, IGEPAL CO-210, IGEPAL CO-520, IGEPAL CO-630, IGEPAL CO-720, IGEPAL CO-890, and IGEPAL DM-970 (available from Aldrich); Triton X-100 (available from Aldrich); BRIJ S10, BRIJ S20, BRIJ 30, BRIJ 52, BRIJ 56, BRIJ 58, BRIJ 72, BRIJ 76, BRIJ 78, BRIJ 92V, BRIJ 97, and BRIJ 98 (available from Aldrich); PLURONIC L-31, PLURONIC L-35, PLURONIC L-61, PLURONIC L-81, PLURONIC L-64, PLURONIC L-121, PLURONIC 10R5, PLURONIC 17R4, and PLURONIC 31R1 (available from Aldrich); Atlas G-5000 and Atlas G-5002L (available from Croda); ATLOX 4912 and ATLOX 4912-SF (available from Croda); and SOLUPLUS (available from BASF), LANEXOL AWS (available from Croda).

Non-limiting examples of cationic surfactants include mono alkyl quaternary amine, fatty acid amide surfactants, amidoamine, imidazoline, and polymeric cationic surfactants.

In some embodiments, the nematicidal composition comprises a co-solvent in addition to water. Non-limiting examples of co-solvents that can be used include ethyl lactate, methyl soyate/ethyl lactate co-solvent blends (e.g., STEPOSOL, available from Stepan), isopropanol, acetone, 1,2-propanediol, n-alkylpyrrolidones (e.g., the AGSOLEX series, available from ISP), a petroleum based-oil (e.g., AROMATIC series and SOLVESSO series available from Exxon Mobil), isoparaffinic fluids (e.g. ISOPAR series, available from Exxon Mobil), cycloparaffinic fluids (e.g. NAPPAR 6, available from Exxon Mobil), mineral spirits (e.g. VARSOL series available from Exxon Mobil), and mineral oils (e.g., paraffin oil).

Examples of commercially available organic solvents include pentadecane, ISOPAR M, ISOPAR V, and ISOPAR L (available from Exxon Mobil). In some embodiments, the nematicidal composition of 3,5-disubstituted-1,3,4-oxadiazol-2(3H)-one may be formulated, mixed in a seed treater tank, combined on the seed by overcoating, or combined with one or more additional active ingredients. The additional active ingredients may comprise, for example, a pesticide or biopesticide. In some embodiments, the nematicidal composition comprises 3,5-disubstituted-1,3,4-oxadiazol-2(3H)-one and another pesticide, for example a nematicide, insecticide, fungicide, herbicide, and/or other chemical.

In some embodiments, the nematicidal composition further comprises a second pesticide (e.g., nematicide, insecticide or fungicide) such as an avermectin (e.g., ivermectin), milbemycin, imidacloprid, aldicarb, oxamyl, fenamiphos, fosthiazate, metam sodium, etridiazole, penta-chloro-nitrobenzene (PCNB), flutolanil, metalaxyl, mefonoxam, and fosetyl-al. Useful fungicides include, but are not limited to, silthiofam, fludioxonil, myclobutanil, azoxystrobin, chlorothalonil, propiconazole, tebuconazole and pyraclostrobin. The composition may also comprise herbicides (e.g., trifloxysulfuron, glyphosate, halosulfuron) and/or other chemicals useful for disease control (e.g., chitosan).

Non-limiting examples of insecticides and nematicides include carbamates, diamides, macrocyclic lactones, neonicotinoids, organophosphates, phenylpyrazoles, pyrethrins, spinosyns, synthetic pyrethroids, tetronic and tetramic acids. In another embodiment, insecticides and nematicides include abamectin, aldicarb, aldoxycarb, bifenthrin, carbofuran, chlorantraniliprole, clothianidin, cyfluthrin, cyhalothrin, cypermethrin, deltamethrin, dinotefuran, emamectin, ethiprole, fenamiphos, fipronil, flubendiamide, fosthiazate, imidacloprid, ivermectin, lambda-cyhalothrin, milbemectin, 3-phenyl-5-(thiophen-2-yl)-1,2,4-oxadiazole, nitenpyram, oxamyl, permethrin, spinetoram, spinosad, spirodichlofen, spirotetramat, tefluthrin, thiacloprid, thiamethoxam, and thiodicarb.

Non-limiting examples of useful fungicides include aromatic hydrocarbons, benzimidazoles, benzothiadiazole, carboxamides, carboxylic acid amides, morpholines, phenylamides, phosphonates, quinone outside inhibitors (e.g. strobilurins), thiazolidines, thiophanates, thiophene carboxamides, and triazoles, Non-limiting examples of fungicides include acibenzolar-5-methyl, azoxystrobin, benalaxyl, bixafen, boscalid, carbendazim, cyproconazole, dimethomorph, epoxiconazole, fluopyram, fluoxastrobin, flutianil, flutolanil, fluxapyroxad, fosetyl-Al, ipconazole, isopyrazam, kresoximmethyl, mefenoxam, metalaxyl, metconazole, myclobutanil, orysastrobin, penflufen, penthiopyrad, picoxystrobin, propiconazole, prothioconazole, pyraclostrobin, sedaxane, silthiofam, tebuconazole, thifluzamide, thiophanate, tolclofos-methyl, trifloxystrobin, and triticonazole.

Non-limiting examples of herbicides include ACCase inhibitors, acetanilides, AHAS inhibitors, carotenoid biosynthesis inhibitors, EPSPS inhibitors, glutamine synthetase inhibitors, PPO inhibitors, PS II inhibitors, and synthetic auxins. Non-limiting examples of herbicides include acetochlor, clethodim, dicamba, flumioxazin, fomesafen, glyphosate, glufosinate, mesotrione, quizalofop, saflufenacil, sulcotrione, and 2,4-D.

Additional actives may also comprise substances such as, biological control agents, microbial extracts, plant growth activators or plant defense agents. Non-limiting examples of biological control agents include bacteria, fungi, beneficial nematodes, and viruses.

In certain embodiments, the biological control agent can be a bacterium of the genus *Actinomycetes, Agrobacterium, Arthrobacter, Alcaligenes, Aureobacterium, Azobacter, Bacillus, Beijerinckia, Brevibacillus, Burkholderia, Chromobacterium, Clostridium, Clavibacter, Comamonas, Corynebacterium, Curtobacterium, Enterobacter, Flavobacterium, Gluconobacter, Hydrogenophaga, Klebsiella, Methylobacterium, Paenibacillus, Pasteuria, Photorhabdus, Phyllobacterium, Pseudomonas, Rhizobium, Serratia, Sphingobacterium, Stenotrophomonas, Variovorax*, and *Xenorhabdus*. In particular embodiments the bacteria is selected from the group consisting of *Bacillus amyloliquefaciens, Bacillus cereus, Bacillus firmus, Bacillus, lichenformis, Bacillus pumilus, Bacillus sphaericus, Bacillus subtilis, Bacillus thuringiensis, Chromobacterium suttsuga, Pasteuria penetrans, Pasteuria usage*, and *Pseudomona fluorescens*.

In certain embodiments the biological control agent can be a fungus of the genus *Alternaria, Ampelomyces, Aspergillus, Aureobasidium, Beauveria, Colletotrichum, Coniothyrium, Gliocladium, Metarhizium, Muscodor, Paecilomyces, Trichoderma, Typhula, Ulocladium*, and *Verticillium*. In another embodiment the fungus is *Beauveria bassiana, Coniothyrium minitans, Gliocladium vixens, Muscodor albus, Paecilomyces lilacinus*, or *Trichoderma polysporum*.

In further embodiments the biological control agents can be plant growth activators or plant defense agents including, but not limited to harpin, *Reynoutria sachalinensis*, jasmonate, lipochitooligosaccharides, and isoflavones.

In some embodiments, the nematicidal compositions described herein exhibit measurable nematode-killing activity or result in reduced fertility or sterility in the nematodes such that fewer viable or no offspring result, or compromise the ability of the nematode to infect or reproduce in its host, or interfere with the growth or development of a nematode. The nematicidal composition may also display nematode repellant properties.

For example, the nematicidal compositions described herein may reduce the survival time of adult nematodes relative to unexposed similarly staged adults, e.g., by about 20%, 40%, 60%, 80%, or more. In some embodiments, the nematicidal compositions described herein may cause the nematodes to cease replicating, regenerating, and/or producing viable progeny, e.g., by about 20%, 40%, 60%, 80%, or more. The effect may be apparent either immediately or in successive generations, or both.

The nematicidal compositions described herein can be used to treat diseases or infestations caused by nematodes of the following non-limiting, exemplary genera: *Globodera, Anguina, Ditylenchus, Tylenchorhynchus, Pratylenchus, Radopholus, Hirschmanniella, Nacobbus, Hoplolaimus, Scutellonema, Rotylenchus, Helicotylenchus, Rotylenchulus, Belonolaimus, Heterodera*, other cyst nematodes, *Meloidogyne, Criconemoides, Hemicycliophora, Paratylenchus, Tylenchulus, Aphelenchoides, Bursaphelenchus, Rhadinaphelenchus, Longidorus, Xiphinema, Trichodorus*, and *Paratrichodorus, Dirofilaria, Onchocerca, Brugia, Acanthocheilonema, Aelurostrongylus, Anchlostoma, Angiostrongylus, Ascaris, Bunostomum, Capillaria, Chabertia, Cooperia, Crenosoma, Dictyocaulus, Dioctophyme, Dipetalonema, Dracunculus, Enterobius, Filaroides, Haemonchus, Lagochilascaris, Loa, Manseonella, Muellerius, Necator, Nematodirus, Oesophagostomum, Ostertagia, Parafilaria, Parascaris, Physaloptera, Protostrongylus, Setaria, Spirocerca, Stephanogilaria, Strongyloides, Strongylus, Thelazia, Toxascaris, Toxocara, Trichinella, Trichostrongylus, Trichuris, Uncinaria*, and *Wuchereria*. In some embodiments, the nematicidal compositions described herein are used to treat diseases or infestations caused by nematodes including *Dirofilaria, Onchocerca, Brugia, Acanthocheilonema, Dipetalonema, Loa, Mansonella, Parafilaria, Setaria, Stephanofilaria*, and *Wucheria, Pratylenchus, Heterodera, Meloidogyne*, and *Paratylenchus*. Examples of non-limiting species include: *Ancylostoma caninum, Haemonchus contortus, Trichinella spiralis, Trichurs muris, Dirofilaria immitis, Dirofilaria tenuis, Dirofilaria repens, Dirofilaria ursi, Ascaris suum, Toxocara canis, Toxocara cati, Strongyloides ratti, Parastrongyloides trichosuri, Heterodera glycines, Globodera pallida, Meloidogyne javanica, Meloidogyne incognita*, and *Meloidogyne arenaria, Radopholus similis, Longidorus elongatus, Meloidogyne hapla*, and *Pratylenchus penetrans*.

Having described the embodiments in detail, it will be apparent that modifications and variations of the disclosure are possible without departing from the scope of the appended claims.

EXAMPLES

The following non-limiting examples are provided for further illustration.

Example 1

Nematicidal Efficacy Assay

A miniaturized greenhouse assay was conducted to study the effects of several 3,5-disubstituted-1,3,4-oxadiazol-2 (3H)-one compounds on *Meloidogyne incognita* nematodes.

Cucumber seeds were sprouted for 3 days in moist paper towels. Acceptable sprouts were 3 to 4 cm long, with several lateral roots just emerging. For each trial compound, a stock solution was prepared in a mixture of acetone and TRITON X100 surfactant (412 mg in 500 mL), such that the concentration of the nematicidal test compound was 5 mg/mL. The chemical stock solution was then added to a mixture of deionized water (10 mL) and TRITON X100 (0.015% concentration), and mixed thoroughly to form the test solution.

Each test solution was evaluated in triplicate. Dry sand (10 mL) was added to each vial. Seedlings were planted by tilting the vial and laying the seedling in the correct orientation so that the cotyledons were just above the sand, and then tilting back to cover the radicles with sand. A sample of the test solution (3.3 mL) was then added to each vial, and the vials were placed in racks under fluorescent light banks. The vials were inoculated two days after planting by adding 500 vermiform *M. incognita* eggs to each vial in deionized or spring water (50 μL). The vials were then kept under the fluorescent lamps at ambient room temperature and watered as needed with deionized water (1 mL), usually twice during duration of test.

Harvest of the cucumber plants was performed 10 to 12 days after inoculation by washing sand off the roots. A root gall rating was assigned using the following Gall rating scale (Gall: % root mass galled): 0=0-5%; 1=6-20%; 2=21-50%; and 3=51-100%. For each test solution, the average of the triplicate gall ratings was then calculated and scored: no galls=0.00-0.33; mild galling=0.67-1.33; moderate galling=1.67-2.33; severe galling=2.67-3.00.

The resulting nematicidal activity of the 3,5-disubstituted-1,3,4-oxadiazol-2 (3H)-one compounds is set forth in Table 1A, below. Comparative solutions comprising other commercially available nematicidal compounds were also evaluated as controls.

TABLE 1

Nematicidal activity of 3,5-disubstituted-1,3,4-oxadiazol-2(3H)-ones

| Name | Structure | Formula | 40/8/1 ppm gall ratings* |
|---|---|---|---|
| 3-(4-chlorophenyl)-5-(thiophen-2-yl)-1,3,4-oxadiazol-2(3H)-one | 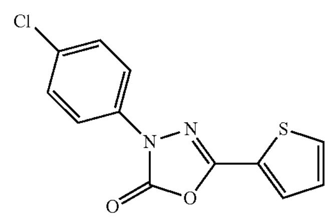 [SMILES: O=c1oc(-c2cccs2)nn1-c1ccc(Cl)cc1] | Ia-iii | 0.00/0.33$^a$/0.00$^a$ |
| 3-phenyl-5-(pyrrol-1-yl)-1,3,4-oxadiazol-2(3H)-one | 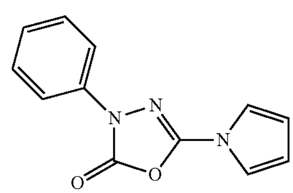 [SMILES: O=c1oc(-n2cccc2)nn1-c1ccccc1] | Ic-i | 0.00/0.33$^b$/3:00$^b$ |
| 3-(4-fluorophenyl)-5-(thiophen-2-yl)-1,3,4-oxadiazol-2(3H)-one | 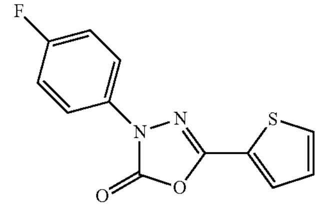 [SMILES: O=c1oc(-c2cccs2)nn1-c1ccc(F)cc1] | Ia-iv | 1.33/2.00/3.00 |
| 3-phenyl-5-(thiophen-2-yl)-1,3,4-oxadiazol-2(3H)-one | 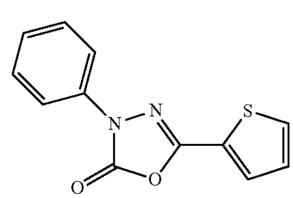 [SMILES: O=c1oc(-c2cccs2)nn1-c1ccccc1] | Ia-i | 1.00/2.00/NTD |

TABLE 1-continued

Nematicidal activity of 3,5-disubstituted-1,3,4-oxadiazol-2(3H)-ones

| Name | Structure | Formula | 40/8/1 ppm gall ratings* |
|---|---|---|---|
| 3-(4-chlorophenyl)-5-(furan-2-yl)-1,3,4-oxadiazol-2(3H)-one | 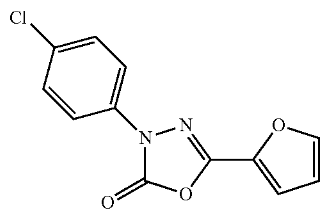 [SMILES: O=c1oc(-c2ccco2)nn1-c1ccc(Cl)cc1] | Ia-v | 0.33/1.00/1.67 |
| 5-(furan-2-yl)-3-phenyl-1,3,4-oxadiazol-2(3H)-one | 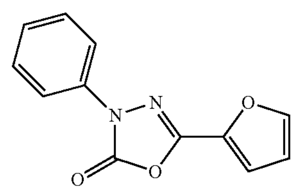 [SMILES: O=c1oc(-c2ccco2)nn1-c1ccccc1] | Ia-ii | 0.00/1.33/3.00 |
| 3-(4-chlorophenyl)-5-(1H-pyrrol-1-yl)-1,3,4-oxadiazol-2(3H)-one | 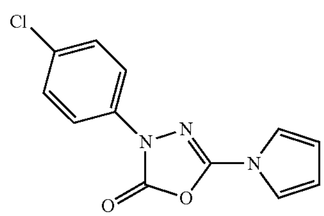 [SMILES: O=c1oc(-n2cccc2)nn1-c1ccc(Cl)cc1] | Ic-ii | 1.00/1.67/2.33 |
| 5-(4-chlorophenyl)-3-(thiophen-2-yl)-1,3,4-oxadiazol-2(3H)-one | 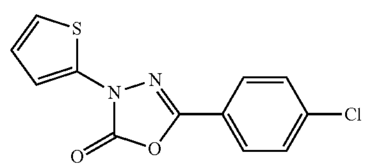 [SMILES: O=c1oc(-c2ccc(Cl)cc2)nn1-c1cccs1] | IIa-iv | 1.00/1.67/3.00 |
| Fenamiphos (1 ppm) | | | 0.00[a] |
| Vydate (1 ppm) | | | 0.67[a] |
| Abamectin (1 ppm) | | | 1.67[b] |

Data with the same letters are taken from the same test.

Example 2

Nematicidal Efficacy Assay

A miniaturized greenhouse assay was conducted to study the effectiveness of 3,5-disubstituted-1,3,4-oxadiazol-2(3H)-one compounds in preventing nematode-related damage to soybean and cucumber plants.

First, a concentrate was prepared by dissolving 2 milligrams of the test compound in 2 mL of an acetone solvent. Test solutions were then prepared by combining an appropriate amount of the concentrate with an aqueous surfactant solution comprising TRITON X100 (0.05%).

Cucumber seeds were planted in a sandy soil mixture in two inch square plastic pots. When the cotyledons were fully opened and just as the first leaf began to emerge, usually 7 days after planting, a nematicidal test solution was applied to each pot. Five milliliters of the appropriate chemical solution was pipetted to the media surface, making sure to avoid contact with the base of the plant. Immediately following chemical application, using a mist nozzle, the pot surface was wetted sufficiently to saturate the pot, effectively watering the test solution into the soil.

Seven days following application of the test solution, each pot was inoculated with root knot nematode (RKN) eggs. A nematode egg slurry was prepared by adding RKN nematode eggs to distilled water to create a concentration of 1000 vermiform eggs per liter of water. A small hole about 1 cm deep was punched into the pot surface, and one milliliter of the nematode egg slurry was pipetted into the hole. Immediately afterwards, the hole was gently covered. Watering of the test plants was then restricted to only water as needed to prevent wilt for a period of 24 hours. After the 24 hour restricted watering, normal sub-irrigation watering was resumed for the duration of the test.

The cucumber plants were rated for root galling 14 days after the egg inoculation. The data in Table 2A, below, are shown as the percent control (i.e., galling reduction) relative to the control blank treatment. A commercially available nematicide, fenamiphos, was also evaluated for comparison.

TABLE 2A

RKN greenhouse soil assay on cucumber plants (7 day longevity test)

| | | Application rate (kg/ha) | |
|---|---|---|---|
| | | 0.25 | 0.1 |
| Name | Structure | Percent Control | |
| 3-(4-chlorophenyl)-5-(thiophen-2-yl)-1,3,4-oxadiazol-2(3H)-one | | 70[a] | 63[a] |
| Fenamiphos | | 94[a] | 80[a] |

Data with the same letters are taken from the same test.

A similar experiment was conducted with regard to control of soybean cyst nematode (SCN) on soybean plants. Soybean seeds were planted in a media consisting of 80% sand and 20% silt loam soil (v/v) in two inch square plastic pots. Treatment with the nematicidal test solution was performed when the soybeans showed the first trifoliate beginning to emerge, approximately 10 to 12 days after planting. Approximately four hours after application of the nematicidal test solution, the nematode soybean cyst nematode (SCN) eggs were applied using the procedure described above. The soybean plants were rated for root galling 28 days after the egg inoculation. Table 2B, below, shows the results of the soil assay.

TABLE 2B

SCN greenhouse sand assay on soybean plants

| | | Application rate (kg/ha)* | |
|---|---|---|---|
| | | 0.25 | 0.1 |
| Name | Structure | Percent Control | |
| 3-(4-chlorophenyl)-5-(thiophen-2-yl)-1,3,4-oxadiazol-2(3H)-one | | 56[a] | 29[a] |
| Oxamyl | | 79[a] | 59[a] |

*Data with the same letters are taken from the same test.

Example 3

Seed Treatment

Experiments were conducted to evaluate the efficacy of 3,5-disubstituted-1,3,4-oxadiazol-2(3H)-one compounds as seed treatments.

200 cucumber seeds were treated with acetone solutions of test compounds at the appropriate concentrations to achieve 0.1 mg/seed, 0.25 mg/seed and 0.5 mg/seed loading. The excess of 30% by weight of test compound was added for each treatment that would equal 130% of the desired rate to assure target seed loading. The test compound (the amount as described in Table 3A below) and surfactant (optional) were dissolved in 3 mL acetone. AGRIMER VA-6 inert polymer was added at a concentration of 15% of the total test compound weight. Seeds were placed in the drum of the batch lab treater. The drum was rotated. The solutions of test compositions as described above were pipette onto seeds. The drum continued to rotate until the seed were dry.

TABLE 3A

Seed Treatment Preparations

| Active Ingredient | Targeted Active Loading (mg/seed) | Active (mg/200 seeds) | Total mg/ seed applied (30% excess) |
|---|---|---|---|
| Formula Ia-iii | 0.1 | 20 | 26 |
| Formula Ia-iii | 0.25 | 50 | 65 |
| Formula Ia-iii | 0.5 | 100 | 130 |

3 inch by 3 inch plastic pots were filled with a media consisting of 80% sand and 20% silt loam soil (v/v). Treated cucumber seeds were planted ½ inch below the soil surface. Pots were watered as needed. Five days after planting the cucumber plants had the first true leaf emerging and each pot was inoculated with 1000 vermiform root knot eggs. The cucumber plants were rated for root galling 14 days after inoculation. The gall ratings were scored on a scale of 0-100 where, 0=no galls and 100=completely galled. Percent control was determined by comparison to the blank (untreated). The results are set forth in Table 3B below.

TABLE 3B

Seed treatment on cucumber for RKN control

| Name | Structure | Application Rate (mg a.i./seed)* | | | |
|---|---|---|---|---|---|
| | | 0.5 | 0.25 | 0.2 | 0.1 |
| | | Percent Control | | | |
| 3-(4-chlorophenyl)-5-(thiophen-2-yl)-1,3,4-oxadiazol-2(3H)-one | 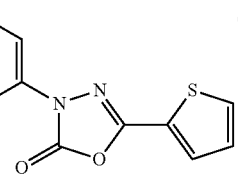 | 62[a] | 25[b] | NT | 12[b] |
| Abamectin | | NT | NT | 37[a] | NT |

*Data with the same letters are taken from the same test.

Example 4

Description of Synthesis of the Compounds of Formulas Ia and Ib

The compounds of Formula Ia and Ib may be prepared using methods known to those skilled in the art. In some embodiments, 3,5-disubstituted-1,3,4-oxadiazol-2(3H)-ones may be prepared by acylation of a corresponding mono-substituted hydrazine with an acyl chloride, followed with cyclization of the N-substituted-2-carbohydrazide with CDI (carbonyldiimidazole) or phosgene to form the oxadiazolone ring.

For example, the compounds of Formula Ia and Ib can be prepared as illustrated by the exemplary reactions set forth in Scheme 1 or Scheme 2 below.

As shown in Scheme 1 below, the aryl-substituted hydrazine hydrochloride salt 1 is reacted with a strong base to form the corresponding aryl-substituted hydrazine compound 2. Compound 2 is then reacted with the acyl chloride 3 to yield the N-substituted-2-carbohydrazide 4. Intermediate compound 4 is then cyclized with CDI (carbonyldiimidazole) to produce the 3,5-disubstituted-1,3,4-oxadiazole-2(3H)-one product 5.

In Scheme 1 below, substituent X corresponds to phenyl, which may be optionally independently substituted as set forth in Formulas Ia and Ib above. Similarly, substituent Y corresponds to furanyl, thienyl, or n-substituted pyrrolyl, each of which may be substituted as set in detail with respect to Formulas Ia and Ib above.

Scheme 1: Synthetic scheme for the preparation of compounds of Formulas Ia and Ib

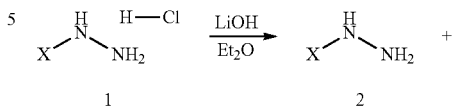

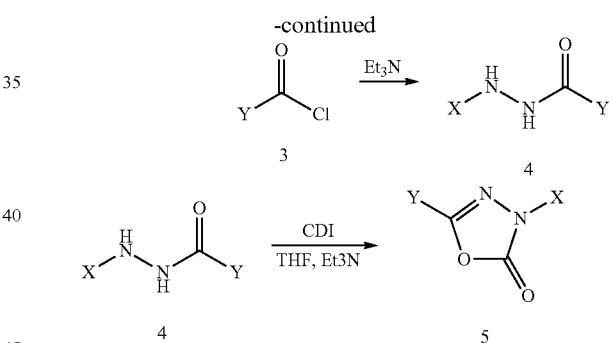

As shown in Scheme 2 below, the mono-substituted hydrazine compound 1 is reacted with the acyl chloride 2 to yield the N-substituted-2-carbohydrazide 3. Intermediate compound 3 is then cyclized with phosgene to produce the 3,5-disubstituted-1,3,4-oxadiazol-2(3H)-one product 4.

In Scheme 2 below, substituent X corresponds to phenyl, which may be optionally independently substituted as set forth in Formulas Ia and Ib above. Similarly, substituent Y corresponds to furanyl, thienyl, or n-substituted pyrrolyl, each of which may be substituted as set in detail with respect to Formulas Ia and Ib above.

Scheme 2: Synthetic scheme for the preparation of compounds of Formulas I and II

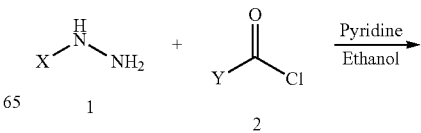

-continued

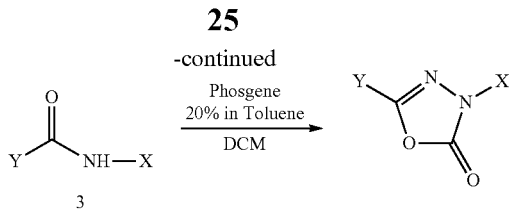

Example 5

Preparation of 3-(4-chlorophenyl)-5-(thiophen-2-yl)-1,3,4-oxadiazol-2(3H)-one (Formula Ia-iii)

A solution of LiOH (2.4 g) in 50 mL water was added to a suspension of 1-(4-chloro-phenyl)hydrazine HCl salt (17.9 g, 100 mmol) in Et$_2$O (300 mL), and the resulting mixture was stirred for 30 minutes. After the mixture became homogenous, the organic layer was separated, and triethylamine (1 eq.) followed by thiophene-2-carbonyl chloride (14.6 g, 100 mmol) were added slowly dropwise at a constant temperature of 0° C. The mixture was stirred for additional 1 hour at room temperature, and then the organic layer was diluted with ethyl acetate (100 mL), washed with brine, and dried over Na$_2$SO$_4$. The crude N'-(4-chlorophenyl)thiophene-2-carbohydrazide (24 g) obtained after the removal of the solvent was used in the next step without further purification.

A mixture of N'-(4-chlorophenyl)thiophene-2-carbohydrazide (20 g, 79.3 mmol), triethylamine (10 mL) and carbonyldiimidazole (16.2 g, 100 mmol) was refluxed in THF (100 mL) for 1 hour. The crude product obtained after the removal of the solvent was triturated with water, filtered, and dried, followed by recrystallization from ethyl acetate/hexanes to provide 3-(4-chloro-phenyl)-5-(thiophene-2-yl)-1,3,4-oxadiazol-2(3H)-one (18 g, 64.7 mmol, yield 81%). The HPLC purity of the final product was 99.9%. LC-MS [M+H] 279.9 (C$_{12}$H$_7$ClN$_2$O$_2$S+H, expected 279.72). The $^1$H-NMR spectrum was in accordance with the chemical structure.

Example 6

Preparation of 3-phenyl-5-(thiophen-2-yl)-1,3,4-oxadiazol-2(3H)-one (Formula Ia-i)

The procedure described in Example 5 above for Formula Ia-iii was followed, starting from phenylhydrazine hydrochloride and thiophene-2-carbonyl chloride, to prepare 18 mg (0.073 mmol, yield 20.3%) of 3-phenyl-5-(thiophen-2-yl)-3H-[1,3,4]oxadiazol-2-one with an HPLC purity of 98.4%. LC-MS [M+H] 245.6 (C$_{12}$H$_8$N$_2$O$_2$S+H, expected 245.27).

Example 7

Preparation of 5-(furan-2-yl)-3-phenyl-1,3,4-oxadiazol-2(3H)-one (Formula Ia-ii)

The procedure described above in Example 5 for Formula Ia-iii was followed, starting from phenylhydrazine as a free based and furan-2-carbonyl chloride, to prepare 3-phenyl-5-(furan-2-yl)-1,3,4-oxadiazol-2(3H)-one (36.2 mg, 0.158 mmol, yield 63%). The HPLC purity of the final product was 99.9%. LC-MS [M+H] 229.6 (C$_{12}$H$_8$N$_2$O$_3$+H, expected 229.21). The $^1$H-NMR spectrum was in accordance with the chemical structure.

Example 8

Preparation of 3-(4-fluorophenyl)-5-(thiophen-2-yl)-1,3,4-oxadiazol-2(3H)-one (Formula Ia-iv)

4-Fluorophenylhydrazine hydrochloride (1.63 g, 10.0 mmol) was mixed with ethanol (150 mL) and pyridine (2.43 mL, 30.0 mmol, 3.0 eq.). The mixture was heated to reflux, and more pyridine (2.43 mL, 30.0 mmol, 3.0 eq.) was added. After stirring for 5 minutes at room temperature, thiophenecarbonyl chloride (10.8 mL, 1.47 g, 10.0 mmol, 1.0 eq.) was added. The suspension was stirred for 2 hours at room temperature, and then at reflux temperature for 30 minutes under a nitrogen atmosphere. Water (375 mL) was added, and the mixture was extracted with ethyl acetate (2×300 mL). The combined organic layers were then washed with brine (100 mL), dried over magnesium sulfate, filtered, and concentrated in vacuo to yield the crude product (2.3 g) as a brown solid. Purification using ISCO flash chromatography (silica, gradient heptanes/ethyl acetate) gave N'-(4-fluorophenyl)thiophene-2-carbohydrazide (575 mg, 2.43 mmol, yield 24.3%) as a brown solid.

N'-(4-fluorophenyl)thiophene-2-carbohydrazide (575 mg, 2.43 mmol) was dissolved in dichloromethane (14 mL) and tetrahydrofuran (10 mL) in a glass flask. The flask was cooled in ice. Phosgene (20% in toluene, 3.42 mL, 6.49 mmol, 2.67 eq.) was added, and the solution was stirred overnight under a nitrogen atmosphere, allowing it to warm to room temperature. Ethyl acetate (40 mL) was added, and the solution was then washed with water (2×25 mL) and brine (25 mL). The solution was dried over magnesium sulfate, filtered and concentrated in vacuo to give 0.59 grams of crude product as a light brown solid. Purification using ISCO flash chromatography (silica, gradient heptanes/ethyl acetate) gave 3-(4-fluorophenyl)-5-(thiophen-2-yl)-1,3,4-oxadiazol-2(3H)-one (210 mg, 0.800 mmol, yield 33.0%) as an off-white solid with an HPLC purity of 99.7%. LC-MS [M+H] 263.02 (C$_{12}$H$_7$FN$_2$O$_2$S+H, expected 263.02). The $^1$H-NMR spectrum was in accordance with the chemical structure.

Example 9

Preparation of 3-(4-chlorophenyl)-5-(furan-2-yl)-1,3,4-oxadiazol-2(3H)-one (Formula Ia-v)

To a suspension of 1-(4-chlorophenyl)hydrazine as the hydrochloride salt (89.5 mg, 0.5 mmol) in Et$_2$O (4 mL) was added a 2 N solution of LiOH (1 mL), and the resulting mixture was stirred for 15 minutes. After the system became homogeneous, the organic layer was separated and dried over Na$_2$SO$_4$. The resulting ethereal solution of carbohydrazide as a free base was cooled to −5° C., and then a solution of furan-2-carbonyl chloride (65 mg, 0.5 mmol) in 5 mL of THF was added dropwise to the resulting mixture. After stirring at 0° C. for 30 minutes, the reaction mixture was diluted with water (50 mL) and extracted with EtOAc (50 mL). The organic layer was then separated, washed with brine, dried over Na$_2$SO$_4$, and evaporated in vacuo. The residue was purified by flash chromatography on silica gel (5-50% EtOAc in hexane) to provide 100 mg (0.382 mmol, yield 76.3%) of 3-(4-chloro-phenyl)-5-furan-2-yl-3H-[1,3,4]oxadiazol-2-one with an HPLC purity of 99.9%. LC-MS [M+H] 263.7 C$_{12}$H$_7$ClN$_2$O$_3$+H, expected 263.01). The $^1$H-NMR spectrum was in accordance with the chemical structure.

Example 10

Preparation of 3-(4-chloro-2-methylphenyl)-5-(furan-2-yl)-1,3,4-oxadiazol-2(3H)-one (Formula Ia-vi)

To a suspension of 1-(4-chloro-2-methylphenyl)hydrazine as the hydrochloride salt (96 mg, 0.5 mmol) in $Et_2O$ (10 mL) was added a 2 N solution of LiOH (3 mL), and the resulting mixture was stirred for 15 minutes. After the system became homogenous, furan-2-carbonyl chloride was added, and the mixture was stirred at room temperature for 30 minutes. The reaction mixture was then diluted with water (100 mL) and extracted with EtOAc (70 mL). The organic layer was separated, washed with brine, and dried over $Na_2SO_4$. The crude material of N'-(4-chloro-2-methylphenyl)furan-2-carbohydrazide obtained after the removal of the solvent was used in the next step without further purification.

A mixture of N'-(4-chloro-2-methylphenyl)furan-2-carbohydrazide (0.5 mmol), triethylamine (0.1 mL, 0.75 mmol), and carbonyldiimidazole (0.24 g, 1.5 mmol) was stirred at 80° C. in 2 mL of THF overnight. The crude product obtained after removal of the solvent was then subject to chromatography (silica gel, 1:9 ethyl acetate-hexanes), followed by crystallization from hexanes to provide 83 mg (0.3 mmol, yield 60%) of 3-(4-Chloro-2-methyl-phenyl)-5-furan-2-yl-3H-[1,3,4]oxadiazol-2-one as a white solid with an HPLC purity of 98.9%. LC-MS [M+H] 277.9 ($C_{13}H_9ClN_2O_3$+H, expected 277.68). The $^1$H-NMR spectrum was in accordance with the chemical structure.

Example 11

Description of Synthesis of the Compounds of Formulas IIa and IIb

The compounds of Formula IIa and IIb may be prepared using methods known to those skilled in the art. For example, the compounds of Formula IIa and IIb may be prepared as illustrated by the exemplary reactions in Schemes 3 and 4 below.

As shown in Scheme 3 below, the aryl-substituted hydrazine hydrochloride salt 1 is reacted with a strong base to form the corresponding aryl-substituted hydrazine compound 2. Compound 2 is then reacted with the acyl chloride 3 to yield the N-substituted-2-carbohydrazide 4. Intermediate compound 4 is they cyclized with CDI (carbonyldiimidazole) to produce the 3,5-disubstituted-1,3,4-oxadiazole-2(3H)-one product 5.

In Scheme 3 below, substituent X corresponds to furanyl, thienyl, or N-substituted pyrrolyl, each of which may be substituted as set in detail with respect to Formulas Ia and Ib above. Similarly, substituent Y corresponds to phenyl, which may be optionally independently substituted as set forth in Formulas Ia and Ib above.

Scheme 3: Synthetic route to compounds of Formula IIa and IIb

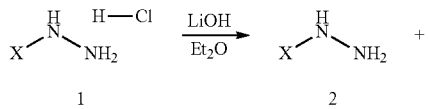

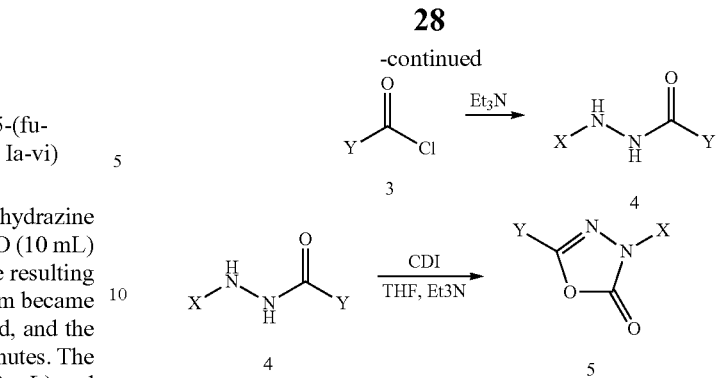

Alternatively, compounds of Formulas IIa and IIb may be prepared as illustrated in Scheme 4. As shown in Scheme 4 below, the substituted hydrazine compound 1 is reacted with the acyl chloride 2 in the presence of triethylamine and tetrahydrofuran to yield the N-substituted-2-carbohydrazide 3. Intermediate compound 3 is then cyclized with phosgene to produce the 3,5-disubstituted-1,3,4-oxadiazole-2(3H)-one product 4.

In Scheme 4 below, substituent X corresponds to furanyl, thienyl, or N-substituted pyrrolyl, each of which may be substituted as set in detail with respect to Formulas Ia and Ib above. Similarly, substituent Y corresponds to phenyl, which may be optionally independently substituted as set forth in Formulas Ia and Ib above.

Scheme 4: Synthetic scheme for the preparation of compounds of Formula IIa

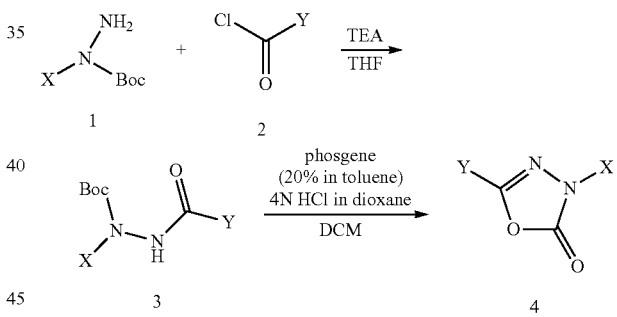

Example 12

Preparation of 5-(4-chlorophenyl)-3-(thiophen-2-yl)-1,3,4-oxadiazol-2(3H)-one (Formula IIa-iv)

To a solution of tert-butyl 1-(thiophen-2-yl)hydrazinecarboxylate (100 mg, 0.467 mmol) in THF (5 mL) was added triethylamine (64 μL, 0.476 mmol, 1 eq.) and 4-chlorobenzoyl chloride (60 μL, 82 mg, 0.467 mmol, 1 eq.), and the resulting mixture was stirred for 1 hour at room temperature. A sample of the reaction mixture (quenched in water, and extracted with EtOAc) showed the presence of the intermediate crude product tert-butyl 2-(4-chlorobenzoyl)-1-(thiophen-2-yl)-hydrazinecarboxylate, as determined by NMR. The reaction mixture was then poured in water and extracted with EtOAc. The organic layer was dried over $MgSO_4$ and concentrated in vacuo. The crude product (278 mg) was purified by automated column chromatography (EtOAc/heptane) to yield tert-butyl 2-(4-chlorobenzoyl)-1-

(thiophen-2-yl)-hydrazinecarboxylate (127 mg, 360 mmol, yield 77%) as a light brown solid with an HPLC purity of greater than 99%. LC-MS (M−1) 351 ($C_{16}H_{17}ClN_2O_3S$-1, expected 352.06).

A solution of tert-butyl 2-(4-chlorobenzoyl)-1-(thiophen-2-yl)-hydrazinecarboxylate (136 mg, 0.385 mmol) in DCM (8 mL) was cooled in an ice-bath. Phosgene (539 μL, 2.66 eq; 20% in toluene) and 4N HCl in dioxane (a few drops) were added, and the mixture was stirred at room temperature for 16 hours. DCM and water were added, and the phases were separated. The aqueous phase was extracted with DCM. The combined organics were dried over $MgSO_4$. Concentration in vacuo yielded a brown solid (96 mg). The crude product was purified by automated column chromatography (EtOAc/Heptane) to yield the desired product (16 mg, 0.057 mmol, yield 15.8%) with an HPLC purity of 98%. LC-MS [M+H] 279.05 ($C_{12}H_7ClN_2O_2S$+H, expected 279.99). The $^1$H-NMR spectrum was in accordance with the chemical structure.

Example 13

Description of Synthesis of the Compounds of Formula Ic

The compounds of Formula Ic may be prepared using methods known to those skilled in the art. For example, the compounds of Formula Ic can be prepared as illustrated by the exemplary reaction set forth in Scheme 5 below.

As shown in Scheme 5 below, the aryl-substituted hydrazine hydrochloride salt 1 is reacted with a strong base to form the corresponding aryl-substituted hydrazine compound 2. Compound 2 is then reacted with the acyl chloride 3 to yield the N-substituted-2-carbohydrazide 4. Intermediate compound 4 is they cyclized with phosgene to produce the 3,5-disubstituted-1,3,4-oxadiazole-2(3H)-one product 5.

In Scheme 1 below, substituent X corresponds to phenyl, which may be optionally independently substituted as set forth in detail in Formula Ic above.

Scheme 5: Synthetic scheme to compounds of the Formula Ic.

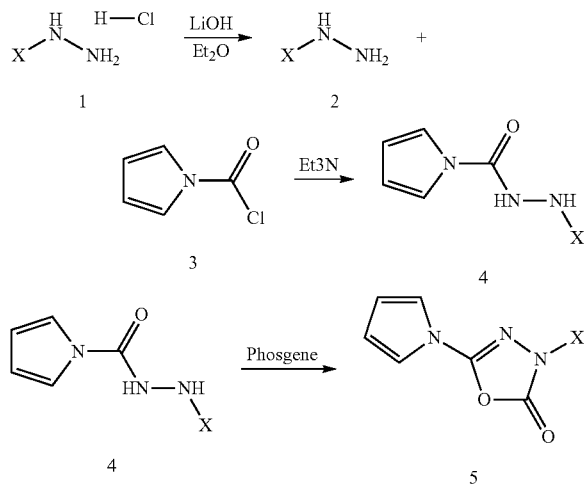

Example 14

Preparation of 3-phenyl-5-(1H-pyrrol-1-yl)-1,3,4-oxadiazol-2(3H)-one (Formula Ic-i)

Phenylhydrazine (86 μL, 1.47 mmol) was dissolved in ethanol (10 mL) and pyridine (211 μL, 2.61 mmol, 3.0 eq.) in a flask, and the mixture was stirred for 20 minutes under a nitrogen atmosphere. The flask was cooled in ice. A solution of 1H-pyrrole-1-carbonyl chloride (1.47 mmol, 1 eq) in tetrahydrofuran (1.5 mL) was added to the mixture. The resulting brown solution was stirred overnight, allowing it to warm to room temperature. Water (60 mL) was added, and the mixture was extracted with ethyl acetate (3×20 mL). The combined organic layers were dried over magnesium sulfate, filtered, and concentrated in vacuo to give 0.18 grams of a dark green solid. Purification by ISCO flash chromatography (silica, gradient heptanes/ethyl acetate) gave two fractions with corresponding N'-phenyl-1H-pyrrole-1-carbohydrazide as a dark green solid (20 mg, HPLC-MS purity 81.7% at 215 nm; 73 mg, HPLC-MS purity 29.5% at 215 nm). Both carbohydrazide fractions were used without further purification and converted to the oxadiazolne as described below in two separate runs.

The first fraction of carbohydrazide (20 mg, 0.099 mmol) was dissolved in dichloromethane (1 mL) and tetrahydrofuran (1.2 mL). The flask was cooled in ice. Phosgene (20% in toluene, 0.137 mL, 0.265 mmol, 2.67 eq) was added, and the solution was stirred overnight under a nitrogen atmosphere, allowing it to warm to room temperature. Ethyl acetate (5 mL) was added, and the solution was washed with water (2×3 mL) and brine (3 mL). The solution was dried over magnesium sulfate, filtered, and concentrated in vacuo to give 39 mg of the crude product as a black tar.

A second fraction of carbohydrazide (73 mg, max 0.363 mmol) was converted into the corresponding oxadiazolone using the same method. The two batches of crude product were combined and purified by ISCO flash chromatography (silica, gradient/heptanes ethyl acetate) to yield 21 mg (0.0924 mmol, yield 20.0%) of 3-phenyl-5-(1H-pyrrol-1-yl)-1,3,4-oxadiazol-2(3H)-one with an HPLC purity of 99.5%. LC-MS [M+H] 228.0 ($C_{12}H_9N_3O_2$+H, expected 228.07). The $^1$H-NMR spectrum was in accordance with the chemical structure.

Example 15

Preparation of 3-(4-chlorophenyl)-5-(1H-pyrrol-1-yl)-1,3,4-oxadiazol-2(3H)-one (Formula Ic-ii)

4-Chlorophenylhydrazine (156 mg, 1.47 mmol) was dissolved in ethanol (10 mL) and pyridine (211 μL, 2.61 mmol, 3.0 eq), and the mixture was stirred for 20 minutes under a nitrogen atmosphere. The flask was cooled in ice. A solution of 1H-pyrrole-1-carbonyl chloride (1.47 mmol, 1 eq) in tetrahydrofuran (1.5 mL) was added. The resulting brown solution was stirred overnight, allowing it to warm to room temperature. Water (60 mL) was added, and the mixture was extracted with ethyl acetate (3×20 mL). The combined organic layers were dried over magnesium sulfate, filtered, and concentrated in vacuo to give 0.27 grams of a dark green solid. Purification by ISCO flash chromatography (silica, gradient heptanes ethyl acetate) gave two fractions with corresponding N'-(4-chlorophenyl)-1H-pyrrole-1-carbohydrazide (149 mg, HPLC-MS purity 62.7% at 215 nm; 25 mg, HPLC-MS purity 23.1% at 215 nm) as a dark green solid. Both carbohydrazide fractions were used without further purification and converted to the oxadiazolone as described below in two separate runs.

The first fraction of carbohydrazide (149 mg, 0.632 mmol) was dissolved in dichloromethane (4 mL) and tetrahydrofuran (3 mL). The flask was cooled in ice. Phosgene (20% in toluene, 0.888 mL, 1.69 mmol, 2.67 eq) was added, and the solution was stirred overnight under a nitrogen atmosphere, allowing it to warm to room temperature. Ethyl acetate (20 mL) was added, and the solution was washed with water (2×10 mL) and brine (10 mL). The solution was dried over magnesium sulfate, filtered, and concentrated in vacuo to give 198 mg of the crude product as a black tar.

A second fraction of the carbohydrazide (25 mg, max 0.106 mmol) was converted into the corresponding oxadiazolone using the same method. The two batches of crude product were combined and purified by ISCO flash chromatography (silica, gradient heptanes/ethyl acetate) to give 3-(4-Chlorophenyl)-5-(1H-pyrrol-1-yl)-1,3,4-oxadiazol-2(3H)-one (19 mg, 0.073 mmol, yield 9.8%) as an off-white solid, with an HPLC purity of 99.4%. LC-MS [M+H] 262.0 ($C_{12}H_8ClN_3O_2$+H, expected 262.03). The $^1$H-NMR spectrum was in accordance with the chemical structure.

When introducing elements herein, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above products and methods without departing from the scope of the invention, it is intended that all matter contained in the above description shall be interpreted as illustrative and not in a limiting sense.

What is claimed is:

1. A compound of Formula I, Formula II, or a salt thereof,

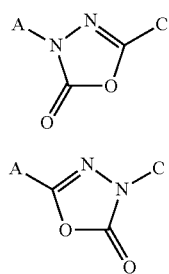

Formula I

Formula II wherein A is selected from the group consisting of phenyl, pyridyl, pyrazyl, oxazolyl, and isoxazolyl, each of which can be optionally independently substituted with one or more substituents selected from the group consisting of halogen, $CF_3$, $CH_3$, $OCF_3$, $OCH_3$, CN, and C(H)O; and C is selected from the group consisting of pyrrolyl, thienyl, furanyl, oxazolyl, and isoxazolyl, each of which can be optionally independently substituted with one or more substituents selected from the group consisting of alkyl, alkoxy, cycloalkyl, haloalkyl, haloalkoxy, heterocyclyl, and halogen, provided that when the compound is a compound of Formula II, C is other than furanyl.

2. The compound of claim 1 wherein A is optionally independently substituted phenyl.

3. The compound of claim 1 wherein C is optionally independently substituted pyrrolyl.

4. The compound of claim 1 wherein C is optionally independently substituted thienyl.

5. The compound of claim 1 wherein C is optionally independently substituted with one or more substituents selected from the group consisting of F, Cl, Br, $CH_3$, and $OCF_3$.

6. The compound of claim 1 wherein the compound is of Formula Ia or a salt thereof,

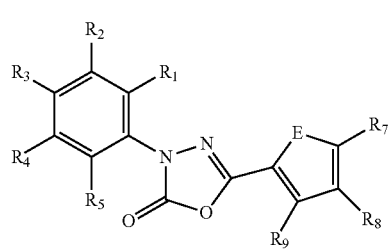

Formula Ia wherein $R_1$ and $R_5$ are independently selected from the group consisting of hydrogen, $CH_3$, F, Cl, Br, $CF_3$, and $OCF_3$;

$R_2$ and $R_4$ are independently selected from the group consisting of hydrogen, F, Cl, Br, and $CF_3$;

$R_3$ is selected from the group consisting of hydrogen, $CH_3$, $CF_3$, F, Cl, Br, $OCF_3$, $OCH_3$, CN, and C(H)O;

$R_7$, $R_8$ and $R_9$ are independently selected from the group consisting of hydrogen, alkyl, alkoxy, cycloalkyl, haloalkyl, haloalkoxy, heterocyclyl, and halogen; and E is selected from the group consisting of O, S, and N—$R_{10}$, wherein $R_{10}$ is alkyl.

7. The compound of claim 6 wherein $R_7$, $R_8$ and $R_9$ are independently selected from the group consisting of hydrogen, F, Cl, Br, $CH_3$, and $OCF_3$.

8. The compound of claim 1 wherein the compound is of Formula Ib or a salt thereof,

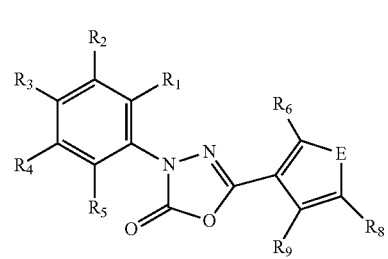

Formula Ib wherein $R_1$ and $R_5$ are independently selected from the group consisting of hydrogen, $CH_3$, F, Cl, Br, $CF_3$, and $OCF_3$;

$R_2$ and $R_4$ are independently selected from the group consisting of hydrogen, F, Cl, Br, and $CF_3$;

$R_3$ is selected from the group consisting of hydrogen, $CH_3$, $CF_3$, F, Cl, Br, $OCF_3$, $OCH_3$, CN, and C(H)O;

$R_6$, $R_8$ and $R_9$ are independently selected from the group consisting of hydrogen, alkyl, alkoxy, cycloalkyl, haloalkyl, haloalkoxy, heterocyclyl, and halogen; and E is selected from the group consisting of O, S, and N—$R_{10}$, wherein $R_{10}$ is alkyl.

9. The compound of claim 8 wherein $R_6$, $R_8$ and $R_9$ are independently selected from the group consisting of hydrogen, F, Cl, Br, $CH_3$, and $OCF_3$.

10. The compound of claim 1 wherein the compound is of Formula Ic or a salt thereof,

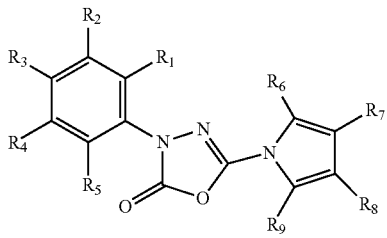

Formula Ic wherein $R_1$ and $R_5$ are independently selected from the group consisting of hydrogen, $CH_3$, F, Cl, Br, $CF_3$, and $OCF_3$;

$R_2$ and $R_4$ are independently selected from the group consisting of hydrogen, F, Cl, Br, and $CF_3$;

$R_3$ is selected from the group consisting of hydrogen, $CH_3$, $CF_3$, F, Cl, Br, $OCF_3$, $OCH_3$, CN, and C(H)O; and $R_6$, $R_7$, $R_8$ and $R_9$ are independently selected from the group consisting of hydrogen, alkyl, cycloalkyl, heterocyclyl, and halogen.

11. The compound of claim 1 wherein the compound is of Formula IIa or a salt thereof,

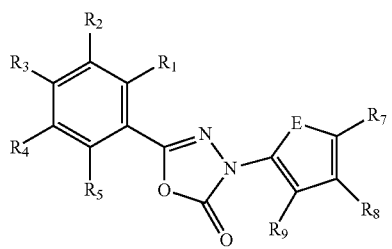

Formula IIa wherein $R_1$ and $R_5$ are independently selected from the group consisting of hydrogen, $CH_3$, F, Cl, Br, $CF_3$, and $OCF_3$;

$R_2$ and $R_4$ are independently selected from the group consisting of hydrogen, F, Cl, Br, and $CF_3$;

$R_3$ is selected from the group consisting of hydrogen, $CH_3$, $CF_3$, F, Cl, Br, $OCF_3$, $OCH_3$, CN, and C(H)O;

$R_7$, $R_8$ and $R_9$ are independently selected from the group consisting of hydrogen, alkyl, alkoxy, cycloalkyl, haloalkyl, haloalkoxy, heterocyclyl, and halogen; and E is selected from the group consisting of S, and N—$R_{10}$, wherein $R_{10}$ is alkyl.

12. The compound of claim 11 wherein $R_7$, $R_8$ and $R_9$ are independently selected from the group consisting of hydrogen, F, Cl, Br, $CH_3$, and $OCF_3$.

13. The compound of claim 1 wherein the compound is of Formula IIb or a salt thereof,

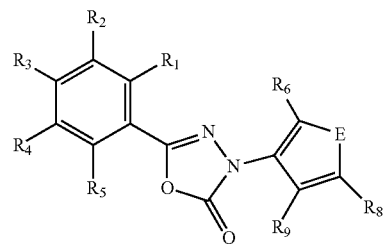

Formula IIb wherein $R_1$ and $R_5$ are independently selected from the group consisting of hydrogen, $CH_3$, F, Cl, Br, $CF_3$, and $OCF_3$;

$R_2$ and $R_4$ are independently selected from the group consisting of hydrogen, F, Cl, Br, and $CF_3$;

$R_3$ is selected from the group consisting of hydrogen, $CH_3$, $CF_3$, F, Cl, Br, $OCF_3$, $OCH_3$, CN, and C(H)O;

$R_6$, $R_8$ and $R_9$ are independently selected from the group consisting of hydrogen, alkyl, alkoxy, cycloalkyl, haloalkyl, haloalkoxy, heterocyclyl, and halogen; and E is selected from the group consisting of S, and N—$R_{10}$, wherein $R_{10}$ is alkyl.

14. The compound of claim 13 wherein $R_6$, $R_8$ and $R_9$ are independently selected from the group consisting of hydrogen, F, Cl, Br, $CH_3$, and $OCF_3$.

15. A compound of claim 1 wherein A is substituted phenyl and C is selected from the group consisting of optionally independently substituted pyrrolyl, thienyl, and furanyl.

16. A compound selected from the group consisting of:
3-phenyl-5-(thiophen-2-yl)-1,3,4-oxadiazol-2(3H)-one,
5-(furan-2-yl)-3-phenyl-1,3,4-oxadiazol-2(3H)-one,
3-(4-chlorophenyl)-5-(thiophen-2-yl)-1,3,4-oxadiazol-2(3H)-one,
3-phenyl-5-(pyrrol-1-yl)-1,3,4-oxadiazol-2(3H)-one,
3-(4-chlorophenyl)-5-(pyrrol-1-yl)-1,3,4-oxadiazol-2(3H)-one,
5-phenyl-3-(thiophen-2-yl)-1,3,4-oxadiazol-2(3H)-one, and 5-(4-chlorophenyl)-3-(thiophen-2-yl)-1,3,4-oxadiazol-2(3H)-one.

17. A nematicidal composition comprising the compound of claim 1.

18. The nematicidal composition of claim 17 further comprising a surfactant.

19. The nematicidal composition of claim 17 further comprising a co-solvent.

20. The nematicidal composition of claim 17 further comprising a biological control agent, microbial extract, plant growth activator or plant defense agent or mixtures thereof.

21. The nematicidal composition of claim 17 further comprising a second pesticide.

22. The nematicidal composition of claim 21 wherein the second pesticide is selected from the group consisting of fungicides, insecticides and herbicides or mixtures thereof.

23. A seed comprising a coating comprising a compound of claim 1.

24. A method of controlling unwanted nematodes, the method comprising administering to a plant, a seed, or soil a composition comprising an effective amount of a compound of Formula I, Formula II, or a salt thereof,

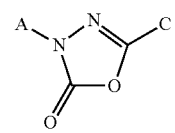

Formula I

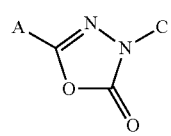

Formula II wherein A is selected from the group consisting of phenyl, pyridyl, pyrazyl, oxazolyl, and isoxazolyl, each of which can be optionally independently substituted with one or more substituents selected from the group consisting of halogen, $CF_3$, $CH_3$, $OCF_3$, $OCH_3$, CN, and C(H)O; and C is selected from the group consisting of pyrrolyl, thienyl, furanyl, oxazolyl, and isoxazolyl, each of which can be optionally independently substituted with one or more substituents selected from the group consisting of alkyl, alkoxy, cycloalkyl, haloalkyl, haloalkoxy, heterocyclyl, and halogen.

25. A method of controlling a nematode infestation or preventing a nematode infestation in an animal, the method comprising administering to an animal a nematicidal treatment composition comprising a compound of Formula I, Formula II, or a salt thereof,

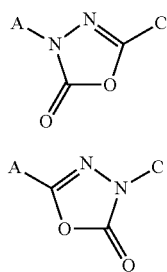

Formula I

Formula II wherein A is selected from the group consisting of phenyl, pyridyl, pyrazyl, oxazolyl, and isoxazolyl, each of which can be optionally independently substituted with one or more substituents selected from the group consisting of halogen, $CF_3$, $CH_3$, $OCF_3$, $OCH_3$, CN, and C(H)O; and C is selected from the group consisting of pyrrolyl, thienyl, furanyl, oxazolyl, and isoxazolyl, each of which can be optionally independently substituted with one or more substituents selected from the group consisting of alkyl, alkoxy, cycloalkyl, haloalkyl, haloalkoxy, heterocyclyl, and halogen.

26. The composition of claim 17, wherein the compound is selected from the group consisting of:
3-phenyl-5-(thiophen-2-yl)-1,3,4-oxadiazol-2(3H)-one,
5-(furan-2-yl)-3-phenyl-1,3,4-oxadiazol-2(3H)-one,
3-(4-chlorophenyl)-5-(thiophen-2-yl)-1,3,4-oxadiazol-2(3H)-one,
3-phenyl-5-(pyrrol-1-yl)-1,3,4-oxadiazol-2(3H)-one,
3-(4-chlorophenyl)-5-(pyrrol-1-yl)-1,3,4-oxadiazol-2(3H)-one,
5-phenyl-3-(thiophen-2-yl)-1,3,4-oxadiazol-2(3H)-one,
and 5-(4-chlorophenyl)-3-(thiophen-2-yl)-1,3,4-oxadiazol-2(3H)-one.

27. The method of claim 24, wherein the compound is selected from the group consisting of:
3-phenyl-5-(thiophen-2-yl)-1,3,4-oxadiazol-2(3H)-one,
5-(furan-2-yl)-3-phenyl-1,3,4-oxadiazol-2(3H)-one,
3-(4-chlorophenyl)-5-(thiophen-2-yl)-1,3,4-oxadiazol-2(3H)-one,
3-phenyl-5-(pyrrol-1-yl)-1,3,4-oxadiazol-2(3H)-one,
3-(4-chlorophenyl)-5-(pyrrol-1-yl)-1,3,4-oxadiazol-2(3H)-one,
5-phenyl-3-(thiophen-2-yl)-1,3,4-oxadiazol-2(3H)-one,
3-(furan-2-yl)-5-phenyl-1,3,4-oxadiazol-2(3H)-one,
and 5-(4-chlorophenyl)-3-(thiophen-2-yl)-1,3,4-oxadiazol-2(3H)-one.

28. The method of claim 25, wherein the compound is selected from the group consisting of:
3-phenyl-5-(thiophen-2-yl)-1,3,4-oxadiazol-2(3H)-one,
5-(furan-2-yl)-3-phenyl-1,3,4-oxadiazol-2(3H)-one,
3-(4-chlorophenyl)-5-(thiophen-2-yl)-1,3,4-oxadiazol-2(3H)-one,
3-phenyl-5-(pyrrol-1-yl)-1,3,4-oxadiazol-2(3H)-one,
3-(4-chlorophenyl)-5-(pyrrol-1-yl)-1,3,4-oxadiazol-2(3H)-one,
5-phenyl-3-(thiophen-2-yl)-1,3,4-oxadiazol-2(3H)-one,
3-(furan-2-yl)-5-phenyl-1,3,4-oxadiazol-2(3H)-one,
and 5-(4-chlorophenyl)-3-(thiophen-2-yl)-1,3,4-oxadiazol-2(3H)-one.

* * * * *